(12) United States Patent
Moody, III et al.

(10) Patent No.: US 11,827,001 B2
(45) Date of Patent: Nov. 28, 2023

(54) NONWOVEN FABRICS WITH ADDITIVE ENHANCING BARRIER PROPERTIES

(71) Applicant: AVINTIV Specialty Materials Inc., Charlotte, NC (US)

(72) Inventors: Ralph A Moody, III, Mooresville, NC (US); Mehmet Selcuk Sinangil, Mooresville, NC (US); Albert G. Dietz, III, Davidson, NC (US); Pierre Grondin, Mooresville, NC (US)

(73) Assignee: AVINTIV Specialty Materials Inc., Charlotte, NC (US)

( * ) Notice: Subject to any disclaimer, the term of this patent is extended or adjusted under 35 U.S.C. 154(b) by 229 days.

(21) Appl. No.: 15/441,780

(22) Filed: Feb. 24, 2017

(65) Prior Publication Data
US 2017/0246832 A1    Aug. 31, 2017

Related U.S. Application Data

(60) Provisional application No. 62/299,821, filed on Feb. 25, 2016.

(51) Int. Cl.
*B32B 5/02*      (2006.01)
*A61F 13/494*    (2006.01)
(Continued)

(52) U.S. Cl.
CPC .............. *B32B 5/022* (2013.01); *A61F 13/15* (2013.01); *A61F 13/494* (2013.01); *A61F 13/51* (2013.01);
(Continued)

(58) Field of Classification Search
CPC ............ B32B 2250/03; B32B 2250/04; B32B 2250/05; B32B 2250/20; B32B 2250/24;
(Continued)

(56) References Cited

U.S. PATENT DOCUMENTS 4,536,361 A    8/1985 Torobin
4,738,677 A    4/1988 Foreman
(Continued)

FOREIGN PATENT DOCUMENTS

CN    105101927 A    11/2015
EP    2626457 B1     3/2015
(Continued)

OTHER PUBLICATIONS

Miao, Menghe Xin, John H. (2018). Engineering of High-Performance Textiles—17.4.6 Nanofiber Nonwoven Membrane Filters for Air Filtration. (pp. 470). Elsevier. Retrieved from https://app.knovel.com/hotlink/pdf/id:kt011GA8G2/engineering-high-performance/nanofiber-nonwoven-membrane (Miao). (Year: 2018).*
(Continued)

*Primary Examiner* — Jennifer A Gillett
(74) *Attorney, Agent, or Firm* — BURR & FORMAN LLP

(57) ABSTRACT

Nonwoven fabrics having liquid barrier properties are provided. The nonwoven fabrics may include one or more nonwoven layers, in which one or more of the nonwoven layers may include a liquid-barrier-enhancing-additive (LBEA) comprising an amide. The nonwoven fabrics may be suitable for use in a wide variety of liquid barrier applications, including facemasks, surgical gowns, surgical drapes, lab coats, and barrier components of absorbent articles (e.g., barrier leg cuffs).

19 Claims, 6 Drawing Sheets

(51) Int. Cl.
| | |
|---|---|
| *A61F 13/15* | (2006.01) |
| *D04H 1/4374* | (2012.01) |
| *D04H 1/42* | (2012.01) |
| *D04H 3/005* | (2012.01) |
| *A61F 13/51* | (2006.01) |
| *B32B 5/26* | (2006.01) |
| *D01F 1/10* | (2006.01) |
| *D01F 6/60* | (2006.01) |
| *D04H 5/06* | (2006.01) |
| *B32B 37/16* | (2006.01) |

(52) U.S. Cl.
CPC ............... *B32B 5/26* (2013.01); *B32B 37/16* (2013.01); *D01F 1/10* (2013.01); *D01F 6/60* (2013.01); *D04H 1/42* (2013.01); *D04H 1/4374* (2013.01); *D04H 3/005* (2013.01); *D04H 5/06* (2013.01); *B32B 2262/0261* (2013.01); *B32B 2305/20* (2013.01); *B32B 2305/28* (2013.01); *B32B 2307/724* (2013.01); *B32B 2307/7265* (2013.01); *B32B 2307/73* (2013.01); *B32B 2377/00* (2013.01); *B32B 2437/00* (2013.01); *B32B 2571/00* (2013.01); *D10B 2401/021* (2013.01); *D10B 2501/04* (2013.01); *D10B 2501/042* (2013.01); *D10B 2505/04* (2013.01); *D10B 2509/00* (2013.01); *D10B 2509/026* (2013.01)

(58) Field of Classification Search
CPC ........ B32B 2250/40; B32B 2307/7265; B32B 2307/73; B32B 2571/00; A61F 13/15; A61F 13/494; D01F 1/10; D01F 6/60; D10B 2505/04; D10B 2501/042; D10B 2501/04; D10B 2509/00; D10B 2401/021; D10B 2509/026
USPC .......................................... 442/381, 382, 392
See application file for complete search history.

(56) References Cited

U.S. PATENT DOCUMENTS

| | | | |
|---|---|---|---|
| 4,795,454 A | | 1/1989 | Dragoo |
| 4,798,602 A | * | 1/1989 | Laus ................. A61F 13/51464 428/500 |
| 5,582,606 A | | 12/1996 | Bruemmer et al. |
| 5,707,735 A | * | 1/1998 | Midkiff ................. D01D 5/253 428/373 |
| 6,110,588 A | | 8/2000 | Perez et al. |
| 6,713,011 B2 | | 3/2004 | Chu et al. |
| 6,740,609 B1 | * | 5/2004 | Peng .......................... D01F 1/10 442/301 |
| 7,435,243 B2 | | 10/2008 | Miyamoto |
| 7,582,247 B2 | | 9/2009 | Armantrout et al. |
| 7,585,437 B2 | | 9/2009 | Jirsak et al. |
| 7,585,451 B2 | | 9/2009 | Bryner et al. |
| 7,618,579 B2 | | 11/2009 | Kim et al. |
| 7,666,343 B2 | | 2/2010 | Johnson et al. |
| 7,902,093 B2 | | 3/2011 | Dharmarajan et al. |
| 8,487,156 B2 | | 7/2013 | Isele et al. |
| 9,205,206 B2 | | 12/2015 | Hamaguchi et al. |
| 2003/0022570 A1 | * | 1/2003 | Santisteban ............... C08K 5/10 442/79 |
| 2005/0039837 A1 | * | 2/2005 | Bevins, III ........ A61F 13/15699 156/62.4 |
| 2005/0073075 A1 | | 4/2005 | Chu et al. |
| 2005/0227564 A1 | * | 10/2005 | Bond ......................... B32B 5/08 442/337 |
| 2006/0012084 A1 | | 1/2006 | Armantrout et al. |
| 2006/0097431 A1 | | 5/2006 | Hovanec |
| 2006/0264130 A1 | | 11/2006 | Karles et al. |
| 2008/0038982 A1 | * | 2/2008 | Motomura ................. B32B 5/26 156/160 |
| 2008/0182468 A1 | * | 7/2008 | Dharmarajan ...... A61F 13/4902 442/101 |
| 2008/0237934 A1 | | 10/2008 | Reneker et al. |
| 2008/0241297 A1 | | 10/2008 | Park |
| 2008/0277836 A1 | | 11/2008 | Park |
| 2009/0148547 A1 | | 6/2009 | Petras et al. |
| 2010/0029162 A1 | * | 2/2010 | Datta ....................... C08L 23/10 442/400 |
| 2011/0003524 A1 | * | 1/2011 | Claasen .................... D04H 3/16 442/329 |
| 2012/0150135 A1 | * | 6/2012 | Tee, Jr. ................ A61F 13/4753 604/372 |
| 2012/0238982 A1 | * | 9/2012 | Weisman .............. A61F 13/537 604/370 |
| 2013/0041335 A1 | * | 2/2013 | Dwiggins ................. B32B 5/26 604/372 |
| 2014/0088535 A1 | * | 3/2014 | Xu ..................... A61F 13/15203 604/366 |
| 2014/0272223 A1 | * | 9/2014 | Cheng .................... B65D 65/38 428/36.1 |
| 2015/0210038 A1 | * | 7/2015 | Ichikawa .................. B32B 7/04 442/364 |

FOREIGN PATENT DOCUMENTS

| | | |
|---|---|---|
| EP | 2626458 B1 | 3/2015 |
| WO | 199847546 A1 | 10/1998 |
| WO | 2016108741 A1 | 7/2016 |

OTHER PUBLICATIONS

Second Written Opinion of the International Preliminary Examining Authority of corresponding International Application No. PCT/US2017/019388 dated Mar. 20, 2018.
International Search Report and Written Opinion of corresponding International Application No. PCT/US2017/019388 dated May 9, 2017.
Communication pursuant to Article 94(3) EPC of European Application No. 17710448.6 dated May 31, 2019.
First Office Action (with translation) issued in corresponding Chinese Patent Application No. 201780025909 dated Aug. 21, 2020.
Second Office Action (with translation) issued in corresponding Chinese Patent Application No. 201780025909.4 dated Mar. 16, 2021.
English translation of Office Action issued in corresponding Colombian Patent Application No. NC2018/0010067 dated Jan. 14, 2021.
English translation of Office Action issued in corresponding Colombian Patent Application No. NC2018/0010067 dated Jul. 7, 2021.

* cited by examiner

NONWOVEN FABRICS WITH ADDITIVE ENHANCING BARRIER PROPERTIES

PRIORITY CLAIM

This application claims priority under 35 U.S.C. § 119(e) to U.S. Provisional Application Ser. No. 62/299,821, filed on Feb. 25, 2016, which is expressly incorporated by reference herein in its entirety.

TECHNICAL FIELD

The presently-disclosed invention relates generally to nonwoven fabrics including a liquid-barrier-enhancing-additive and articles including the same, such as absorbent articles including barrier leg cuffs including such a nonwoven fabric.

BACKGROUND

A range of applications utilize nonwoven fabrics that are hydrophobic and relatively open (e.g., porous) so they are breathable to gases, such as air and water vapor, while resisting penetration by aqueous liquids. The majority of such nonwovens are intended to resist penetration by aqueous fluids and are made from polyolefins (e.g., polypropylene, polyethylene), which are naturally hydrophobic. However, a trend in the industry has been to focus on reducing the cost of such products by reducing the amount of polymer (e.g., polyolefins) used in the manufacturing process. In this regard, there has been significant interest in developing a means to further improve the barrier properties of the material to at least compensate for the down-gauging of the final nonwoven fabrics.

One general approach to improve barrier properties has been to incorporate fluorochemicals either as a melt dispersed additive or as a topical treatment applied to the nonwoven fabric. While this is a typical approach used for the high-end barrier fabrics used for medical applications (e.g., surgeon gowns or operating drapes), this approach is costly and is not always an economical solution for less demanding applications.

Therefore, there remains a need for cost effective nonwoven fabrics that provide enhanced resistance to penetration to liquids, which may be suitable for a use in a wide variety of liquid barrier applications.

SUMMARY OF INVENTION

One or more embodiments of the invention may address one or more of the aforementioned problems. Certain embodiments according to the invention provide nonwoven fabrics including one or more nonwoven layers, in which at least one of the nonwoven layers includes a liquid-barrier-enhancing-additive (LBEA) comprising an amide. In this regard, nonwoven fabrics according to certain embodiments of the invention provide barrier nonwoven fabrics that exhibit improved liquid barrier properties over identically constructed comparative nonwoven fabrics being devoid of a LBEA. For instance, the LBEA (e.g., one or more LBEAs) may be added into a polymer melt used to form a plurality of filaments forming one or more of the nonwoven layers of a nonwoven fabric in accordance with certain embodiments of the invention. In accordance with certain embodiments of the invention, one or more of the nonwoven layers may comprise continuous and/or staple fibers, which may independently include one or more LBEAs. Such nonwoven fabrics may be suitable for a wide variety of liquid barrier applications, including, for example, facemasks, surgical gowns, surgical drapes, lab coats, or barrier components of absorbent articles (e.g., barrier leg cuffs).

In one aspect, for instance, the present invention provides nonwoven fabrics including one or more nonwoven layers, in which at least one of the one or more nonwoven layers comprises a LBEA comprising an amide. The LBEA, in accordance with certain embodiments of the invention, may comprise a primary amide, a secondary amide, a tertiary amide, a bis-amide, or any combination thereof.

In another aspect, the present invention provides articles including a nonwoven fabric including at least one LBEA as disclosed herein. In accordance with certain embodiments of the invention, the article may comprise a facemask, a surgical gown, a surgical drape, a lab coat, a filter, or an absorbent article. In accordance with certain embodiments of the invention, the article may comprise an absorbent article, such as a diaper comprising at least one barrier leg cuff including a nonwoven fabric comprising at least one LBEA as disclosed herein.

In yet another aspect, the present invention provides a method of forming a nonwoven fabric as disclosed herein. In accordance with certain embodiments of the invention, the method of forming a nonwoven fabric may comprise a step of forming a polymer melt comprising a LBEA comprising an amide and another step of forming one or more nonwoven layers from the polymer melt to provide the nonwoven fabric. In accordance with certain embodiments of the invention, the method may also comprise melt-spinning the polymer melt to form a plurality of meltspun filaments.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout, and wherein.

DETAILED DESCRIPTION

Figure 1:
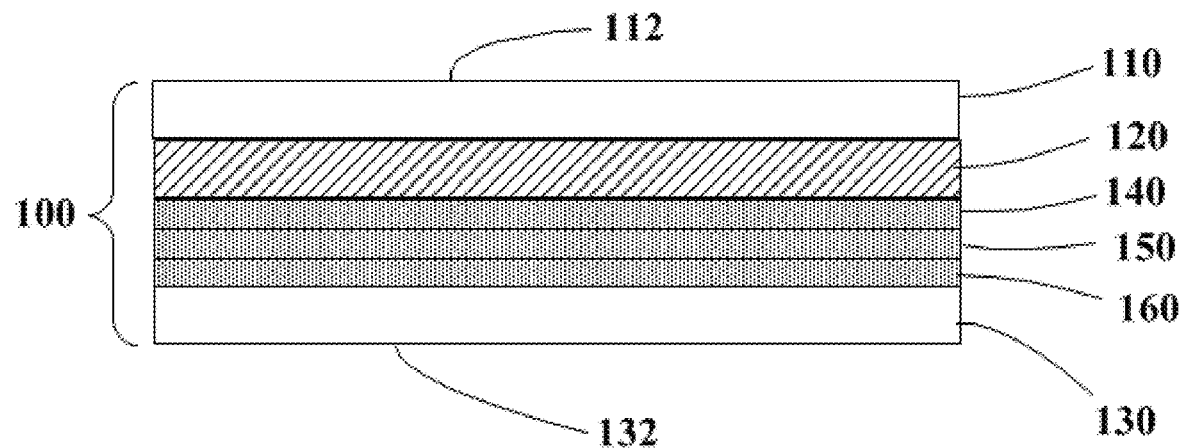
FIG. 1 illustrates a nonwoven fabric according to one embodiment of the invention.

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The invention includes, according to certain embodiments, nonwoven fabrics including one or more nonwoven layers, in which at least one of the nonwoven layers includes a liquid-barrier-enhancing-additive (LBEA) comprising an amide. In this regard, nonwoven fabrics according to certain embodiments of the invention provide barrier nonwoven fabrics that exhibit improved liquid barrier properties over identically constructed comparative nonwoven fabrics being devoid of a LBEA. For instance, the LBEA (e.g., one or more LBEAs) may be added into a polymer melt used to form a plurality of filaments and/or fibers forming one or more of the nonwoven layers of a nonwoven fabric in accordance with certain embodiments of the invention. For example, nonwoven fabrics (e.g., barrier nonwoven fabrics) according to certain embodiments of the invention may comprise a single stand-alone nonwoven layer (e.g., a meltblown layer, a spunbond layer, etc.) comprising one or more LBEAs or a multilayer nonwoven fabric (or composite) comprising a plurality of nonwoven layers bonded together (e.g., via thermal, mechanical, and/or adhesive bonding) in which one or more of the plurality of nonwoven layers may include one or more LBEAs. Additionally, a stand-alone nonwoven layer comprising one or more LBEAs may comprise fine fibers, as discussed below, such as those produced by a meltblown process. Such a stand-alone nonwoven layer may optionally be combined with a reinforcement layer, which provides added strength for handling. One or more of the nonwoven layers may comprise continuous filaments and/or staple fibers, which may independently include one or more LBEAs. Nonwoven fabrics, in accordance with certain embodiments of the invention, may comprise enhanced liquid barrier properties allowing them to be particularly suitable for a wide variety of liquid barrier applications, including, for example, facemasks, surgical gowns, surgical drapes, lab coats, or barrier components of absorbent articles (e.g., barrier leg cuffs).

The terms "substantial" or "substantially" may encompass the whole amount as specified, according to certain embodiments of the invention, or largely but not the whole amount specified according to other embodiments of the invention.

The terms "polymer" or "polymeric", as used interchangeably herein, may comprise homopolymers, copolymers, such as, for example, block, graft, random, and alternating copolymers, terpolymers, etc., and blends and modifications thereof. Furthermore, unless otherwise specifically limited, the term "polymer" or "polymeric" shall include all possible structural isomers; stereoisomers including, without limitation, geometric isomers, optical isomers or enantionmers; and/or any chiral molecular configuration of such polymer or polymeric material. These configurations include, but are not limited to, isotactic, syndiotactic, and atactic configurations of such polymer or polymeric material. The term "polymer" or "polymeric" shall also include polymers made from various catalyst systems including, without limitation, the Ziegler-Natta catalyst system and the metallocene/single-site catalyst system.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process conventionally known in the art such as, for example, meltblowing processes, spunbonding processes, hydroentangling, electro-blown, electro-spinning, air-laid, and bonded carded web processes.

The term "layer", as used herein, may comprise a generally recognizable combination of similar material types and/or functions existing in the X-Y plane.

The term "staple fiber", as used herein, may comprise a cut fiber from a filament. In accordance with certain embodiments of the invention, any type of filament material may be used to form staple fibers. For example, staple fibers may be formed from synthetic polymeric fibers and/or elastomeric fibers. Examples of materials may comprise polyamides, polyesters, polypropylene, and polyethylene terephthalate. The average length of staple fibers may comprise, by way of example only, from about 2 centimeters to about 15 centimeters.

The term "spunbond", as used herein, may comprise fibers which are formed by extruding molten thermoplastic material as filaments from a plurality of fine, usually circular, capillaries of a spinneret with the diameter of the extruded filaments then being rapidly reduced. According to an embodiment of the invention, spunbond fibers are generally not tacky when they are deposited onto a collecting surface and may be generally continuous. It is noted that the spunbond used in certain composites of the invention may include a nonwoven described in the literature as SPIN-LACE®.

The term "meltblown", as used herein, may comprise fibers formed by extruding a molten thermoplastic material through a plurality of fine die capillaries as molten threads or filaments into converging high velocity, usually hot, gas (e.g. air) streams which attenuate the filaments of molten thermoplastic material to reduce their diameter, which may be to microfiber or sub-microfiber diameter, according to certain embodiments of the invention. According to an embodiment of the invention, the die capillaries may be circular. Thereafter, the meltblown fibers are carried by the high velocity gas stream and are deposited on a collecting surface to form a web of randomly disbursed meltblown fibers. Meltblown fibers are typically microfibers and can be sub-microfibers which may be continuous or discontinuous and are generally tacky when deposited onto a collecting surface.

As used herein, the terms "consolidation" and "consolidated" may comprise the bringing together of at least a portion of the fibers of a nonwoven web into closer proximity or attachment there-between (e.g., fused together) to form a bonding site, or bonding sites, which function to increase the resistance of the nonwoven to external forces (e.g., abrasion and tensile forces), as compared to the unconsolidated web. The bonding site or bonding sites, for example, may comprise a discrete or localized region of the web material that has been softened or melted and optionally subsequently or simultaneously compressed to form a discrete or localized deformation in the web material. Furthermore, the term "consolidated" may comprise an entire nonwoven web that has been processed such that at least a portion of the fibers are brought into closer proximity or attachment there-between (e.g., fused together), such as by thermal bonding as merely one example. Such a web may be considered a "consolidated nonwoven" according to certain embodiments of the invention. Additionally, a specific, discrete region of fibers that is brought into close proximity or attachment there-between (e.g., fused together), such as an individual bond site, can be described as "consolidated".

In accordance with certain embodiments of the invention, consolidation may be achieved by methods that apply, for example, heat and/or pressure to the fibrous web (e.g., nonwoven web) via one or more embossing rolls or using a stream of hot fluid (e.g., through-air bonding). One non-limiting and exemplary method comprises thermal bonding. Thermal bonding can be accomplished by passing the fibrous web (e.g., nonwoven web) through a pressure nip formed by two rolls, one of which comprising an embossing roll which may be heated and contain a plurality of raised protrusions having one or more geometric shapes (e.g., points, diamond shaped, circular, elliptical, dog-bone shaped, etc.) on its surface which impart or form corresponding discrete thermal bond sites on the fibrous web (e.g., nonwoven web). Such an operating step, for example, may be referred to as "calendering" or "embossing" in which the nonwoven web is drawn between an embossing roll having an embossing pattern allowing only part of the web to become exposed to heat and pressure and a second roll (e.g., an anvil roll). The degree or extent of consolidation may be expressed as a percentage of the total surface area of the web that has been consolidated or subjected to consolidation and may be referred to as a "bonding area" or "consolidation area". Stated somewhat differently, the terms "bonding area" and "consolidated area", as used interchangeably herein, may comprise the area per unit area occupied by the localized sites formed by bonding the fibers into bond sites and may be expressed as a percentage of the total unit area of the consolidated nonwoven. For example, consolidated nonwovens (e.g., subjected to thermal bonding via an embossing roll) may comprise a plurality of discrete, spaced-apart bond sites or points (e.g., perimeter and internal bond sites or points) formed by bonding only the fibers of the nonwoven web in the area of localized energy input. Fibers or portions of fibers remote from the localized energy input remain substantially unbonded to adjacent fibers.

The term "bicomponent fibers", as used herein, may comprise fibers formed from at least two different polymers extruded from separate extruders but spun together to form one fiber. Bicomponent fibers are also sometimes referred to as conjugate fibers or multicomponent fibers. The polymers are arranged in a substantially constant position in distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement, each as is known in the art of multicomponent, including bicomponent, fibers. The "bicomponent fibers" may be thermoplastic fibers that comprise a core fiber made from one polymer that is encased within a thermoplastic sheath made from a different polymer or have a side-by-side arrangement of different thermoplastic fibers. The first polymer often melts at a different, typically lower, temperature than the second polymer. In the sheath/core arrangement, these bicomponent fibers provide thermal bonding due to melting of the sheath polymer, while retaining the desirable strength characteristics of the core polymer. In the side-by-side arrangement, the fibers shrink and crimp creating z-direction expansion.

I. Barrier Nonwoven Fabrics

In one aspect, the invention provides nonwoven fabrics (e.g., liquid barrier nonwoven fabrics) including one or more nonwoven layers, in which at least one of the one or more nonwoven layers comprises one or more liquid-barrier-enhancing-additives (LBEAs). In accordance with certain embodiments of the invention, the LBEA may comprise an amide. The LBEA, in accordance with certain embodiments of the invention, may comprise a primary amide, a secondary amide, a tertiary amide, a bis-amide, or any combination thereof. In accordance with certain embodiments of the invention, the one or more LBEAs may comprise one or more primary amides. By way of example, primary amides suitable as an LBEA in accordance with certain embodiments of the invention comprise erucamide, oleamide, strearamide, behenamide, or any combination thereof. Alternatively or additionally, certain embodiments of the invention may comprise one or more LBEAs comprising one or more secondary amides. By way of example, secondary amides suitable as an LBEA in accordance with certain embodiments of the invention comprise oleyl palmitamide, strearyl erucamide, or any combination thereof. Alternatively or additionally, certain embodiments of the invention may comprise one or more LBEAs comprising one or more bis-amides, such as ethylene bis-amides. By way of example, bis-amides suitable as an LBEA in accordance with certain embodiments of the invention comprise ethylene bis-strearamide, ethylene bis-oleamide, or any combination thereof.

LBEAs, in accordance with certain embodiments of the invention, may comprise an amide (e.g., a primary amide, a secondary amide, a tertiary amide, bis-amide, etc.) including one or more saturated or unsaturated aliphatic chains. In accordance with certain embodiments of the invention, the one or more aliphatic chains may each independently comprise from about 1 to about 30 carbon atoms (e.g., about 5 to about 30 carbon atoms). For example, a secondary amides and bis-amides may comprise two saturated and/or unsaturated carbon chains the may each independently comprise from about 1 to about 30 carbon atoms (e.g., about 5 to about 30 carbon atoms). By way of example only, the one or more aliphatic chains may each independently comprise from at least about any of the following: 1, 5, 10, 15, 16, 17, 18, 19, 20, 21, 22, 23, 24, and 25 carbon atoms and/or at most about 30, 29, 28, 27, 26, 25, 20, and 15 carbon atoms (e.g., about 15 to about 25 carbon atoms, about 20 to 30 carbon atoms, etc.). Moreover, all whole number end points that can create a smaller range within a given range disclosed herein are within the scope of certain embodiments of the invention. By way of example, the foregoing disclosure of about 10 to about 30 carbon atoms includes the disclosure of intermediate ranges, for example, of: from about 10 to about 12 carbon atoms; from about 18 to about 25 carbon atoms; from about 5 to about 23 carbon atoms. In accordance with certain embodiments of the invention, the LBEA may comprise an amide including an unsaturated aliphatic chain having one or more elements or unsaturation. An element of unsaturation corresponds to two fewer hydrogen atoms than in the saturated formula. For example, a single double bound accounts for one element of unsaturation, while a triple bond would account for two elements of unsaturation. In accordance with certain embodiments of the invention, the LBEA includes an unsaturated aliphatic chain comprising from about 1 to about 10 elements of unsaturation (e.g., 1, 2, 3, 4, 5, 6, 7, 8, 9, or 10 elements of saturation).

In according with certain embodiments of the invention, the LBEA may comprise an amide comprising a decomposition temperature, as measured by thermogravimetric analysis (TGA), that exceeds processing temperatures associated with formation of the fibers including the LBEA(s). By way of a brief background, TGA can measure the temperature at which a material (e.g., chemical compound) begins to lose weight rapidly due to, for example, breakdown into volatile by-products or simply volatilization of the material (e.g., chemical compound). As an example of how to conduct this TGA, the weight of a sample is measured when exposed in a chamber under nitrogen atmosphere and the temperature is raised from 25° C. to 450° C. at a ramp up speed of 20° C./min. A weight loss of 5% by weight and up to 10% by weight can be set as the point where a chemical compound (e.g., a sample) starts to lose weight rapidly. In this regard, for example, a decomposition temperature of the LBEA may comprise the temperature at which the LBEA starts to lose weight rapidly (e.g., after a LBEA weight loss of 10% by weight in accordance with certain embodiments of the invention or after a LBEA weight loss of 5% by weight in accordance with certain embodiments of the invention). In accordance with certain embodiments of the invention, the LBEA may comprise a decomposition temperature, as measured by TGA and as described above, comprising at least about 200° C., at least about 220° C., at least about 230° C., at least about 240° C., at least about 250° C., at least about 260° C., at least about 280° C., at least about 300° C., at least about 320° C., at least about 340° C., at least about 360° C., at least about 370° C., at least about 380° C., at least about 400° C., at least about 410° C., or at least about 420° C. The decomposition temperature of the LBEA, for example, may comprise from at least about any of the following: 200° C., 220° C., 230° C., 240° C., 250° C., 260° C., 270° C., 280° C., 300° C., 320° C., 340° C., 350° C., 360° C., and 370° C. and/or at most about 500° C., 480° C., 460° C., 440° C., 420° C., 410° C., 400° C., 380° C., 360° C., and 340° C. (e.g., about 220° C. to about 360° C., about 260° C. to about 400° C., etc.) as measured by TGA and as described above. Moreover, all whole number end points that can create a smaller range within a given range disclosed herein are within the scope of certain embodiments of the invention. By way of example, the foregoing disclosure of about 300° C. to about 320° C. includes the disclosure of intermediate ranges, for example, of from about 305° C. to about 310° C.

In accordance with certain embodiments of the invention, the LBEA may comprise a molecular weight (g/mol) of at least about any of the following: 270, 280, 285, 290, 295, 300, 310, 320, 330, 335, 340, and 350 g/mol and/or at most about 650, 625, 600, 590, 580, 570, 560, 550, 525, 500, 475, 450, 425, 400, and 375 g/mol (e.g., about 280 g/mol to about 590 g/mol, about 335 g/mol to about 590 g/mol, etc.). Moreover, all whole number end points that can create a smaller range within a given range disclosed herein are within the scope of certain embodiments of the invention. By way of example, the foregoing disclosure of about 335 g/mol to about 600 g/mol includes the disclosure of intermediate ranges, for example, of from about 337 g/mol to about 589 g/mol.

In accordance with certain embodiments of the invention, the nonwoven fabric may comprise a stand-alone nonwoven layer comprising a LBEA or a multilayer nonwoven fabric (or composite) including a plurality of nonwoven layers, in which one or more of the plurality of nonwoven layers comprises at least one LBEA. In accordance with certain embodiments of the invention, for instance, the nonwoven fabric may comprise a plurality of nonwoven layers including a first nonwoven layer comprising a plurality of first layer fibers having a first average fiber diameter and a second nonwoven layer comprising a plurality of second layer fibers having a second average fiber diameter, in which the first average fiber diameter is larger than the second average fiber diameter. In this regard, the average fiber diameter or effective fiber diameter (for fibers having a non-round cross section) may vary between nonwoven layers within the nonwoven fabric. For instance, certain embodiments of the invention may further comprise a third nonwoven layer comprising a plurality of third layer fibers having a third average fiber diameter, in which the third average fiber diameter is larger than the second average fiber diameter. In this regard, the first average fiber diameter may be the same or different than the third average fiber diameter. By way of example only, the second average fiber diameter may comprise fine fibers having an average fiber diameter (or average effective diameter for non-round fibers) from about 0.1 to about 10 microns (e.g., about 0.1 to about 5 microns, about 0.1 to about 3 microns, about 0.1 to about 2 microns, etc.). Moreover, all whole number end points and/or single decimal (e.g., numbers reported to the nearest tenth) end points that can create a smaller range within a given range disclosed herein are within the scope of certain embodiments of the invention. By way of example, the foregoing disclosure of about 0.1 to about 2 microns includes the disclosure of intermediate ranges, for example, of: from about 0.2 to about 2 microns; from about 0.5 to about 1 micron; from about 0.5 to about 2 microns; from about 1 to about 2 microns; etc. In accordance with certain embodiments of the invention, for example, each of the first average fiber diameter (or average effective diameter for non-round fibers) of the first nonwoven layer and the third average fiber diameter (or average effective diameter for non-round fibers) of the third nonwoven layer may independently comprise from about 10 to about 30 microns (e.g., about 10 to about 25 microns, about 12 to about 25 microns, about 12 to about 20 microns, etc.). Moreover, all whole number end points that can create a smaller range within a given range disclosed herein are within the scope of certain embodiments of the invention. By way of example, the foregoing disclosure of about 10 to about 30 microns includes the disclosure of intermediate ranges, for example, of: from about 10 to about 11 microns; from about 10 to about 12 microns; from about 10 to about 13 microns; etc. In accordance with certain embodiments of the invention, the first average fiber diameter of the first nonwoven layer and the third average fiber diameter (or average effective diameter for non-round fibers) of the third nonwoven layer may independently comprise from at least about 0.6 denier to about 4 denier (e.g., about 0.8 to about 4 denier, about 1 to about 4 denier, about 1.2 to about 3 denier, etc.). Moreover, all whole number end points and/or single decimal (e.g., numbers reported to the nearest tenth) end points that can create a smaller range within a given range disclosed herein are within the scope of certain embodiments of the invention. By way of example, the foregoing disclosure of about 1 to about 4 denier includes the disclosure of intermediate ranges, for example, of: from about 1 to about 2 deniers; from about 1 to about 3 deniers; from about 2 denier to about 3 deniers; from about 2 deniers to about 4 deniers; from about 3 to about 4 deniers.

In accordance with certain embodiments of the invention, the second nonwoven layer may comprise an interior portion of the nonwoven fabric and be directly or indirectly sandwiched between the first nonwoven layer and the third nonwoven layer. For example, the second nonwoven layer may be in direct contact with both the first nonwoven layer and the third nonwoven layer, in direct contact with only one of the first nonwoven layer or the third nonwoven layer, or in direct contact with one or more intermediate layers positioned between the second nonwoven layer and the first nonwoven layer and/or third nonwoven layer. In accordance with certain embodiments of the invention, the first nonwoven layer may define a first outermost layer of the nonwoven fabric and the third nonwoven layer may define a second outermost layer of the nonwoven fabric. In accordance with certain embodiments of the invention, for example, the first nonwoven layer, the third nonwoven layer, or both may comprise continuous fibers and/or staple fibers. For example, the first nonwoven layer, the third nonwoven layer, or both may comprise a spunbond nonwoven independently having round cross sectional fibers or non-round cross-sectional fibers, or a combination thereof. In this regard, the first nonwoven layer may comprise a plurality of first layer fibers comprising spunmelt fibers comprising a round cross-section and/or a non-round cross-section. In accordance with certain embodiments of the invention, for instance, the plurality of first layer fibers may comprise spunmelt fibers comprising a non-round cross-section including a longest cross-sectional dimension defining an effective fiber diameter of the spunmelt fibers of the first layer fibers. By way of example, the spunmelt fibers of the first nonwoven layer may comprise a ribbon-shaped cross-section, a multilobal cross-section, or any combination thereof. A multilobal cross-section may, for example, comprise a trilobal cross-section, a star-shaped cross-section, or any combination thereof. In a similar manner, the third nonwoven layer may comprise a plurality of third layer fibers comprising spunmelt fibers comprising a round cross-section and/or a non-round cross-section. In accordance with certain embodiments of the invention, for instance, the plurality of third layer fibers may comprise spunmelt fibers comprising a non-round cross-section including a longest cross-sectional dimension defining an effective fiber diameter of the spunmelt fibers of the third layer fibers. By way of example, the spunmelt fibers of the third nonwoven layer may comprise a ribbon-shaped cross-section, a multilobal cross-section, or any combination thereof. A multilobal cross-section may, for example, comprise a trilobal cross-section, a star-shaped cross-section, or any combination thereof. In accordance with certain embodiments of the invention, the first nonwoven layer, the third nonwoven layer, or both may comprise non-continuous fibers (e.g., staple fibers) comprising a round cross-section and/or a non-round cross-section.

The fibers of individual nonwoven layers, in accordance with certain embodiments of the invention, may comprise a homogeneous composition or they may comprise zones of different composition, examples of the latter being multi-component fibers. Multicomponent fibers may comprise a sheath/core, pie, island-in the-sea, or side-by-side configuration. As noted above, the fibers may also comprise a cross-section of different shapes, such as round, trilobal, ribbon, star-shape, other multilobal shapes, or hollow. The cross-sectional shapes of the fibers may be produced by the exit shape of the capillaries used to spin those fibers. For example, ribbon-shaped fibers and their production have been described in EP2626458B1 and EP2626457B1, the contents of which are each incorporated by reference herein to the extent that such disclosures are consistent with the present disclosure.

The composition for forming the fibers or phases of a fiber, in accordance with certain embodiments of the invention, for any of the nonwoven layers of the nonwoven fabric may comprise a polymer or a blend of polymers, as well as additional additives (e.g., pigments, UV stabilizers, etc.) commonly used in the production of fibers or filaments. In certain embodiments of the invention, the one or more nonwoven layers may independently comprise a synthetic polymer, for example any thermoplastic polymer that is compatible with the one or more LBEAs. In accordance with certain embodiments of the invention, the synthetic polymer may comprise a polyolefin, a polyester, a polyamide, or any combination thereof. In accordance with certain embodiments of the invention, the polymer comprises a polyolefin. Examples of suitable polyolefin polymers include a polyethylene, a polypropylene, a copolymer thereof, or other forms of those polymers or blends of those polymers. For example, a polyethylene may comprise a low density polyethylene, a linear low density polyethylene, a medium density polyethylene, a high density polyethylene, or copolymers where ethylene is a major component. Furthermore, such polyethylene polymers may be made with Ziegler-Natta, metallocene, or other catalytic systems or other processes. In certain embodiments of the invention, for example, the polypropylene may comprise a polypropylene homopolymer and a polypropylene copolymer. In accordance with certain embodiments of the invention, the polypropylene may comprise a form comprising an isotactic form, a syndiotactic form, or an atactic form. The polypropylene may comprise polypropylenes made with Ziegler-Natta or metallocene catalyst systems or any other suitable process.

In accordance with certain embodiments of the invention, the polymer composition used for forming the filaments and/or fibers comprises a polypropylene. For the production of continuous fibers, the polypropylene may comprise a viscosity as measured by the MFR test method that is between 8 and 100 (e.g., between 20 and 40). The MFR test method referred to pertains to the results achieved by testing the polymer composition by the standard test method ASTM D1238 performed at a temperature of 230° C. and with a weight of 2.16 kg. For the production of fine fibers, for example, the polypropylene may comprise a MFR that is greater than 300, such as greater than 1000 when tested on the fibers that are produced by the process. Some polypropylene may be vis-broken during the extrusion process, which is the reason for referencing measurement on the fibers rather than the polymeric feedstock.

In accordance with certain embodiments of the invention, the synthetic polymer may comprise at least one of a polyethylene, a polypropylene, a partially aromatic or fully aromatic polyester, an aromatic or partially aromatic polyamide, an aliphatic polyamide, or any combination thereof.

In accordance with certain embodiments of the invention, the second nonwoven layer may comprise a meltblown nonwoven. The plurality of second layer fibers, in accordance with certain embodiments of the invention, may alternatively or additionally comprise spunblown fibers, melt film fibrillated fibers, electro-blown fibers, electro-spun fibers, or any combination thereof. In this regard, the second layer fibers, according to certain embodiments of the invention, may comprise fine fibers as discussed above and have an average diameter (or effective diameter) of less than about 5 microns, less than about 4 microns, or less than about 2 microns, in which these fibers may be produced according to meltblown or other processes known by one of ordinary skill in the art. Examples of those other processes may include melt film fibrillation, electro-blowing, or electro-spinning. Melt film fibrillation, for example, consists of extruding a film of polymer and fibrillating it with high speed air. Suitable and non-limiting examples of melt film fibrillation include U.S. Pat. No. 4,536,361 to Torobin, U.S. Pat. No. 6,110,588 to Perez et al., and U.S. Pat. No. 7,666,343 to Johnson et al., each of which is incorporated herein by reference. Electro-blowing comprises feeding a polymeric solution to a spinning nozzle to which a high voltage is applied while compressed gas is used to envelop the polymer solution in a forwarding gas stream as it exits the nozzle, and collecting the resulting nanofiber web on a grounded suction collector. Suitable and non-limiting examples of electro-blowing methods include U.S. Pat. No. 7,582,247 to Armantrout et al, U.S. Pat. No. 7,585,451 to Bryner et al, U.S. Pat. No. 7,618,579 to Kim et al, U.S. Publication No. 2006/0097431 to Hovanec, U.S. Publication No. 2006/0012084 to Armantrout et al, and U.S. Publication No. 2005/0073075 to Chu et al., each of which is incorporated herein by reference. Electro-spinning employs an electrostatic force to draw a charged liquid polymeric formulation from a source to a collector. An electrostatic field is used to accelerate the liquid formulation from the source to the collector on which the fibers are collected. Suitable and non-limiting examples of electro-spinning methods for making fibers as described herein have been described in U.S. Pat. No. 7,585,437 to Jirsak et al., U.S. Pat. No. 6,713,011 to Chu et al., US. Publication No. 2008/0237934 to Reneker et al, U.S. Publication Nos. 2008/0277836 and 2008/0241297, to Park, US. Publication No. 2009/0148547 to Petras et al, and U.S. Publ. No. 2006/0264130 to Karles, et al., each of which is incorporated herein by reference.

In accordance with certain embodiments of the invention, the nonwoven fabric may comprise a fourth nonwoven layer comprising sub-micron fibers (e.g., fibers having a diameter of less than 1 micron). The fourth nonwoven layer may be directly or indirectly sandwiched between the first nonwoven layer and the third nonwoven layer in accordance with certain embodiments of the invention. The sub-micron fibers may be produced according to one or more of the previously described methods for forming fibers, such as melt film fibrillation, electro-blowing, electro-spinning, or any combination thereof.

In accordance with certain embodiments of the invention, one or more of the first nonwoven layer, the second nonwoven layer, the third nonwoven layer, or the fourth nonwoven layer if present, may comprise one or more LBEAs. In accordance, with certain embodiments of the invention, each of the nonwoven layers may comprise one or more LBEAs.

As noted above, nonwoven fabrics according to certain embodiments of the invention may comprise a plurality of nonwoven layers that have been bonded or consolidated together. Such multilayer nonwoven fabrics (or composites) may comprise a variety of constructions formed from a variety of nonwoven web forming processes. By way of example only, the nonwoven fabrics according to certain embodiments of the invention may comprise a variety of structures including SMS, SMMS, SSMMS, SSMMMS, RSMMR or RSMMMR, in which 'S' stands for a layer of continuous fibers with round cross-sections that are produced by the spunbond process; 'R' stands for a layer of fibers with ribbon-shaped cross-sections that are also produced by the spunbond process; and 'M' is a layer of fine fibers (as discussed above) made by the meltblown process or made by other process comprising spunblown, melt film fibrillation, electro-blown, electro-spun, or other process known to those of ordinary skill in the art. As noted above, the outermost layers may comprise an average fiber diameter (or average effective diameter) that may be larger than the average fiber diameter (or average effective diameter) of one or more of the 'M' layers. One or more LBEAs may be added to one or more of the 'S', 'M', and/or 'R' layers.

In accordance with certain embodiments of the invention, for instance, the nonwoven fabric may comprise a construction according to one of the following formulae:

$$S1_a\text{-}M_b\text{-}N_c\text{-}S2_d; \quad \text{(I)}$$

$$R1_a\text{-}M_b\text{-}N_c\text{-}R2_d; \quad \text{(II)}$$

wherein
'S1' comprises a spunbond nonwoven or a staple fiber-containing nonwoven (e.g., a carded nonwoven) comprising round cross-sectional fibers;
'S2' comprises a spunbond nonwoven or a staple fiber-containing nonwoven (e.g., a carded nonwoven) comprising round cross-sectional fibers;
'M' comprises a meltblown nonwoven;
'N' comprises a fine fiber containing nonwoven (e.g., a micron or sub-micron fiber containing nonwoven) prepared by a method other than meltblowing;
'R1' comprises a spunbond nonwoven comprising non-round cross-sectional fibers or a staple fiber-containing nonwoven (e.g., a carded nonwoven) comprising non-round cross-sectional fibers;
'R2' comprises a spunbond nonwoven comprising non-round cross-sectional fibers or a staple fiber-containing nonwoven (e.g., a carded nonwoven) comprising non-round cross-sectional fibers;
the subscripts 'a', 'b', 'c', and 'd' each denote the number of layers for a given type of material (e.g., '$R1_a$' describes a material including 'a' number of adjacent layers identified as R1), wherein
'a' is independently selected from 1-5 (e.g., 1, 2, 3, 4, or 5);
'b' is independently selected from 0-8 (e.g., 0, 1, 2, 3, 4, 5, 6, 7, or 8);
'c' is independently selected from 0-3 (e.g., 0, 1, 2, or 3);
'd' is independently selected from 1-5 (e.g., 1, 2, 3, 4, or 5).

In accordance with certain embodiments of the invention, the sum or 'b'+'c' comprises a value of at least one (1). Moreover, all whole number end points for subscripts 'a', 'b', 'c', and 'd' that can create a smaller range within a given range disclosed herein are within the scope of certain embodiments of the invention. By way of example, the foregoing disclosure 'a' being from 1 to about 5 layers includes the disclosure of intermediate ranges, for example, of: from about 1 to 4 layers; from 1 to 3 layers; from 1 to 2 layers; etc. In accordance with certain embodiments of the invention, nonwoven fabrics according to any of the foregoing constructions may comprise one or more LBEAs in one or more nonwoven layers (e.g., all nonwoven layers, only the outermost layers, only one or more interior layers, etc.)

In accordance with certain embodiments, for instance, the nonwoven fabric may comprise a construction according to the following formula:

$$(R1_a\text{-}S1_b \text{ or } S1_b\text{-}R1_a)\text{-}M_c\text{-}N_d\text{-}(R2_e\text{-}S2_f \text{ or } S2_f\text{-}R2_e); \quad \text{(III)}$$

wherein
- 'R1' comprises a spunbond nonwoven comprising non-round cross-sectional fibers or a staple fiber-containing nonwoven (e.g., a carded nonwoven) comprising non-round cross-sectional fibers;
- 'R2' comprises a spunbond nonwoven comprising non-round cross-sectional fibers or a staple fiber-containing nonwoven (e.g., a carded nonwoven) comprising non-round cross-sectional fibers;
- 'S1' comprises a spunbond nonwoven or a staple fiber-containing nonwoven (e.g., a carded nonwoven) comprising round cross-sectional fibers;
- 'S2' comprises a spunbond nonwoven or a staple fiber-containing nonwoven (e.g., a carded nonwoven) comprising round cross-sectional fibers;
- 'M' comprises a meltblown nonwoven;
- 'N' comprises a fine fiber containing nonwoven (e.g., a micron or sub-micron fiber containing nonwoven) prepared by a method other than meltblowing;
- the subscripts 'a', 'b', 'c', 'd', 'e', and 'f' each denote the number of layers for a given type of material (e.g., 'R1$_a$' describes a material including 'a' number of adjacent layers identified as R1), wherein
- 'a' is independently selected from 1-5 (e.g., 1, 2, 3, 4, or 5);
- 'b' is independently selected from 1-5 (e.g., 1, 2, 3, 4, or 5);
- 'c' is independently selected from 0-8 (e.g., 0, 1, 2, 3, 4, 5, 6, 7, or 8);
- 'd' is independently selected from 0-3 (e.g., 0, 1, 2, or 3);
- 'e' is independently selected from 1-5 (e.g., 1, 2, 3, 4, or 5); and
- 'f' is independently selected from 1-5 (e.g., 1, 2, 3, 4, or 5).

In accordance with certain embodiments of the invention, the sum or 'c'+'d' comprises a value of at least one (1). Moreover, all whole number end points for subscripts 'a', 'b', 'c', 'd', 'e', and 'f' that can create a smaller range within a given range disclosed herein are within the scope of certain embodiments of the invention. By way of example, the foregoing disclosure 'a' being from 1 to about 5 layers includes the disclosure of intermediate ranges, for example, of: from about 1 to 4 layers; from 1 to 3 layers; from 1 to 2 layers; etc. In accordance with certain embodiments of the invention, nonwoven fabrics according to any of the foregoing constructions may comprise one or more LBEAs in one or more nonwoven layers (e.g., all nonwoven layers, only the outermost layers, only one or more interior layers, etc.)

As noted above, nonwoven fabrics in accordance with certain embodiments of the invention may comprise a plurality of nonwoven layers including two outermost layers and one or more interior layers located between the two outermost layers. In accordance with certain embodiments of the invention, either one or both of the two outermost layers may comprise one or more LBEAs and the one or more interior layers may be devoid of a LBEA. In other embodiments according to the invention, at least one of the one or more interior layers may comprise one or more LBEAs and the two outermost layers may be devoid of a LBEA.

FIG. 1, for example, illustrates a nonwoven fabric 100 according to one embodiment of the invention. As shown in FIG. 1, the nonwoven fabric 100 includes first nonwoven layer 110 comprising a spunbond nonwoven layer having round fibers and defining a first outermost surface 112. The nonwoven fabric 100 also includes a second nonwoven layer 120 comprising a spunbond nonwoven layer having non-round fibers and being positioned adjacent the first nonwoven layer 110. The nonwoven fabric 100 also includes a third nonwoven layer 130 comprising a spunbond nonwoven layer having round fibers and defining a second outermost surface 132. The particular embodiment illustrated in FIG. 1 also includes three (3) intermediate meltblown nonwoven layers 140, 150, 160. In accordance with certain embodiments of the invention, the nonwoven fabric 100 may comprise one or more LBEA in one or more of the nonwoven layers 110, 120, 130, 140, 150, 160 (e.g., all nonwoven layers, only the outermost layers, only one or more interior layers, etc.).

Figure 2:
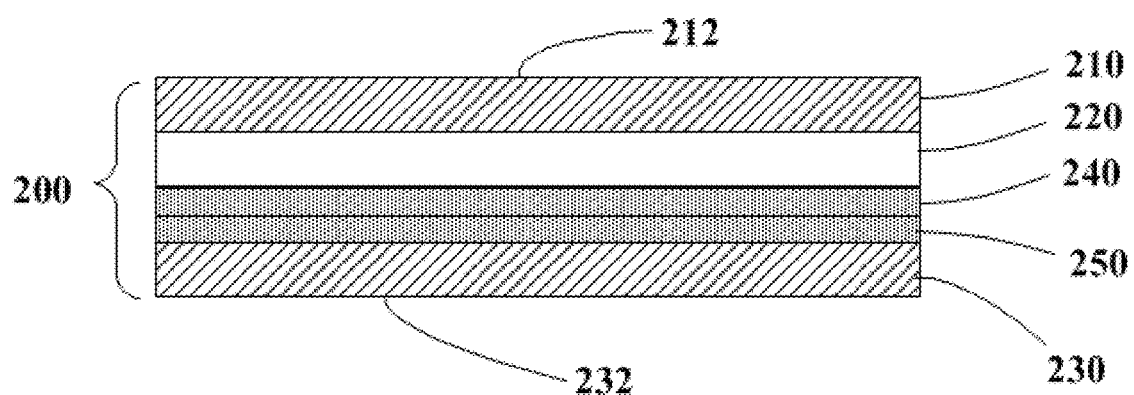
FIG. 2 illustrates also illustrates a nonwoven according to one embodiment of the invention.

FIG. 2 illustrates another embodiment in accordance with the invention, in which the nonwoven fabric 200 includes a first nonwoven layer 212 comprising a spunbond nonwoven layer having non-round fibers and defining a first outermost surface 212. The nonwoven fabric 200 also includes a second nonwoven layer 220 comprising a spunbond nonwoven layer having round fibers and being positioned adjacent the first nonwoven layer 210. The nonwoven fabric 200 of FIG. 2 also includes a third nonwoven layer 230 comprising a spunbond nonwoven layer having non-round fibers and defining a second outermost surface 232. The particular embodiment illustrated in FIG. 2 also includes two (2) intermediate meltblown nonwoven layers 240, 250. In accordance with certain embodiments of the invention, the nonwoven fabric 200 may comprise one or more LBEAs in one or more of the nonwoven layers 210, 220, 230, 240, 250 (e.g., all nonwoven layers, only the outermost layers, only one or more interior layers, etc.).

In accordance with certain embodiments of the invention, the nonwoven fabric may comprise one or more nonwoven layers and as previously noted any one or all of the nonwoven layers of the nonwoven fabric may comprise one or more LBEAs. In this regard, the plurality of fibers forming an individual nonwoven layer may comprise, in accordance with certain embodiments of the invention, one or more LBEAs from about 0.05% by weight of the fibers to about 10% by weight of the fibers (e.g., 0.05 to 8% by weight of the fibers, 0.05 to 6% by weight of the fibers, etc.). In accordance with certain embodiments of the invention, the plurality of fibers forming an individual nonwoven layer may comprise one or more LBEAs from at least about any of the following: 0.05%, 0.08%, 1.0%, 1.5%, 2.0%, 2.5%, and 3.0% by weight of the fibers and/or at most about 10%, 8%, 6%, 5%, 4%, and 3% by weight of the fibers (e.g., about 1-3% by weight of the fibers, about 2-5% by weight of the fibers, etc.). Moreover, all whole number end points and/or single decimal (e.g., numbers reported to the nearest tenth) end points that can create a smaller range within a given range disclosed herein are within the scope of certain embodiments of the invention. By way of example, the foregoing disclosure of about 1 to about 10% by weight of the fibers includes the disclosure of intermediate ranges, for example, of: from about 1 to about 2% by weight of the fibers; from about 1 to about 2.5% by weight of the fibers; from about 1 to about 3% by weight of the fibers; etc. In this regard, any layer or layers comprising a LBEA may independently comprise a weight percentage of one or more LBEAs according to any of the foregoing ranges.

In accordance with certain embodiments of the invention, the nonwoven fabric may be consolidated or bonded by a variety of bonding mechanisms, such as a thermal bonding operation, a mechanical bonding operation, an adhesive bonding operation, or any combination thereof. In accordance with certain embodiments of the invention, the bonding of the nonwoven fabric may comprise thermal bonding with a calendar, an ultrasonic bonding system, or hot fluid (e.g. through-air bonding). Mechanical bonding, in accordance with certain embodiments of the invention, may comprise mechanical entanglement of fibers by different methods, such as needle-felting or hydro-entanglement.

In accordance with certain embodiments of the invention, the nonwoven fabrics including one or more LBEAs exhibit improved liquid barrier properties (e.g., resistance to penetration by a fluid). Nonwoven fabrics according to certain embodiments of the invention, for example, comprise an increased low surface tension strike through (LSTST) value that is greater than that of a comparative nonwoven fabric having the same construction except for being devoid of a LBEA and/or a mean flow pore diameter (MFPD) (i.e., a measurement of the average pore size of the composite) value that is smaller than that of a comparative nonwoven fabric having the same construction except for being devoid of a LBEA. In this regard, a larger LSTST value realized by certain embodiments of the invention indicates an increase in liquid barrier properties to aqueous fluids. At the same time, when a nonwoven fabric includes a LBEA, in accordance with certain embodiments of the invention, a slight reduction in MFPD is typically realized as well as reduction in air permeability. These modifications to the MFPD and air permeability may further facilitate an increase in liquid barrier properties.

In accordance with certain embodiments of the invention, as noted above, the nonwoven fabric may comprise at least one layer including non-round fibers, such as ribbon fibers. The barrier-enhancing impact of one or more LBEA in such non-round fibers (e.g., continuous fibers) may be greater than the barrier-enhancing impact in similar round fibers having the same amount of the one or more LBEAs therein according to certain embodiments of the invention. In this regard, a larger increase in liquid barrier properties (e.g., LSTST) may be realized in non-round fibers as compared to similarly sized round fibers, in which all fibers comprise the same amount of LBEA.

The barrier-enhancing impact of one or more LBEAs, according to certain embodiments of the invention, may be greater for smaller diameter fibers (e.g., fine meltblown fibers) than for larger fiber diameters of the same construction. In certain embodiments of the invention, for example, a larger LSTST value for a meltblown nonwoven layer formed from a reduced production throughput may be realized as compared to a comparative meltblown nonwoven layer formed from the same material but formed at a larger or faster throughput. For instance, meltblown fibers made at lower throughputs may generally comprise smaller average diameters than if they were formed at a higher throughput. In accordance with certain embodiments of the invention, a larger increase in liquid barrier properties (e.g., LSTST) may be realized in smaller diameter fibers as compared to larger diameter fibers formed from the same process (e.g., meltblowing process), in which all fibers comprise the same amount of LBEA (e.g., same weight percentage of LBEA in the fibers). In this regard, certain embodiments according to the invention may comprise one or more nonwoven layers comprising fine fibers (e.g., from about 1 micron to about 4 microns) as discussed above and/or one or more sub-micron fiber containing nonwoven layers as discussed above, in which one or more of fine fibers and/or sub-micron fibers comprise one or more LBEAs. For example, a meltblown web including a LBEA (e.g., erucamide) exhibits improved barrier properties for a web made of only meltblown as demonstrated by the difference between the time a drop of an aqueous solution takes to penetrate a nonwoven layer made with a LBEA (e.g., erucamide) and a similar nonwoven layer made without a LBEA. Accordingly, the incorporation of a meltblown layer comprising, for example, fine fibers as discussed above may be beneficially incorporated into a multilayer nonwoven fabric (or composite) as described above (SMS, SMMS, etc.)

Although not wishing to be held to the following theory, the one or more LBEAs may bloom with time to the surface of the fibers and modify their coefficient of friction. Without being limited by the theory, it is hypothesized that while the LBEA (e.g., erucamide) blooms at the surface of the fibers (e.g., continuous fibers) it may also transfer to the fibers of adjacent nonwoven layers (e.g., interior meltblown fibers). The apparent transfer of a LBEA (e.g., erucamide) to fibers of an adjacent nonwoven layer (e.g., interior meltblown fibers) may affect advantageously the resistance to wettability of those fibers as well as impacting the pore size of the network formed by, for example, interior meltblown fibers. This theory appears to be supported by the realization of a reduction in air permeability as well as MFPD. Finally as the MFPD is further reduced by having finer, for example, meltblown fibers (e.g., by making them at lower throughput), the LBEA (e.g., erucamide)-containing nonwoven fabrics exhibit higher barrier properties as compared to identically constructed nonwoven fabrics being devoid of a LBEA. Additionally, the increased level of barrier-enhancing impact realized by fine fibers (as compared to the impact realized in a larger diameter fiber) and non-round fibers (as compared to the impact realized in a round diameter fiber) including a LBEA (e.g., erucamide) supports the hypothesis. In this regard, the greater surface area associated with non-round fibers (e.g., ribbon fibers) and/or fine fibers (as opposed to comparatively more coarse fibers) may comprise greater surface interaction and/or contact with the LBEA (e.g., erucamide) bloomed to the surface of the fibers.

In accordance with certain embodiments of the invention, the nonwoven fabric may comprise an air permeability comprising a value that is from about 5% to about 30% less than that of a comparative nonwoven fabric having the same construction except for being devoid of the LBEA. In accordance with certain embodiments of the invention, the nonwoven fabric may comprise an air permeability comprising a value that is at least about any of the following: 5%, 6%, 8%, 10%, 12%, and 15% less than that of a comparative nonwoven fabric having the same construction except for being devoid of the LBEA and/or at most about 30%, 25%, 20%, 18%, and 15% less than that of a comparative nonwoven fabric having the same construction except for being devoid of the LBEA. In accordance with certain embodiments of the invention, the air permeability of the nonwoven fabric, for example, may comprise from about 25 (m/min) to about 80 (m/min) (e.g., from about 30 to about 70 (m/min)). In accordance with certain embodiments of the invention, the air permeability of the nonwoven fabric may comprise from at least about any of the following: 20, 25, 30, 35, 40, 45, and 50 (m/min) and/or at most about 80, 75, 70, 65, 60, 55, and 50 (m/min).

In accordance with certain embodiments of the invention, the nonwoven fabric may comprise a MFPD comprising a value that is from about 1% to about 10% smaller than a comparative nonwoven fabric having the same construction except for being devoid of the LBEA. In accordance with certain embodiments of the invention, the nonwoven fabric may comprise a MFPD comprising a value that is at least about any of the following: 1%, 2%, 3%, 4%, 5%, and 6% smaller than a comparative nonwoven fabric having the same construction except for being devoid of the LBEA and/or at most about 15%, 12%, 10%, 8%, and 6% smaller than a comparative nonwoven fabric having the same construction except for being devoid of the LBEA. In accordance with certain embodiments of the invention, the MFPD of the nonwoven fabric may comprise from about 5 microns to about 30 microns (e.g., from about 10 microns to about 30 microns). In accordance with certain embodiments of the invention, the MFPD of the nonwoven fabric may comprise from at least about any of the following: 5, 6, 8, 10, 12, and 15 microns and/or at most about 30, 25, 20, 18, and 15 microns.

Additionally or alternatively, the nonwoven fabric may comprise a LSTST value that is from about 10% to about 60% greater than a comparative nonwoven fabric having the same construction except for being devoid of the LBEA. In accordance with certain embodiments of the invention, the nonwoven fabric may comprise a LSTST value that is from at least about any of the following: 10%, 12%, 15%, 20%, and 25% greater than a comparative nonwoven fabric having the same construction except for being devoid of the LBEA and/or at most about 70%, 60%, 55%, 50%, 40%, 30%, and 25% greater than a comparative nonwoven fabric having the same construction except for being devoid of the LBEA. In accordance with certain embodiments of the invention, the LSTST value of the nonwoven fabric may comprise from about 10 to about 40 seconds (e.g., from about 12 to about 20 seconds). In accordance with certain embodiments of the invention, the LSTST value of the nonwoven fabric may comprise from at least about any of the following: 10, 12, 15, 20, 25, 30, 35, and 40 seconds and/or at most about 90, 80, 70, 60, 50, 40, 35, 30, 25, 20, and 15 seconds.

Nonwoven fabrics according to certain embodiments of the invention may comprise a barrier ratio between the MFPD to the LSTST value comprising from about 1:2 to about 2:1. In accordance with certain embodiments of the invention, the barrier ratio between the MFPD to the LSTST value may comprise from at least about any of the following: 1:2, 1:1.8, 1:1.6, 1:1.4, 1:1.2, and 1:1 and/or at most about 2:1, 1.8:1, 1.6:1, 1.4:1, 1.2:1, and 1:1 (e.g., from about 1:1.6 to about 1.2:1, etc.). In accordance with certain embodiments of the invention, the barrier ratio may comprises from about 1:2 to about 1:1, and the MFPD of the nonwoven fabric may comprises from about 10 microns to about 15 microns. The barrier ratio, in accordance with certain embodiments of the invention, may comprise from about 1:0.8 (or 1.25:1) to about 1:0.5 (or 2:1), and the MFPD of the nonwoven fabric may comprise from about 17 microns to about 25 microns. In accordance with certain embodiments of the invention, the barrier ratio may comprise from about 1:0.9 (or 1.11:1) to about 1:0.5 (or 2:1), and the MFPD of the nonwoven fabric may comprise from about 16 microns to about 25 microns.

In accordance with certain embodiments of the invention, a magnitude of change of the barrier ratio may increase with decreasing MFPD of the nonwoven fabric given the same amount of LBEA present in the nonwoven fabric. Additionally or alternatively, a magnitude of change of the LSTST may increase with decreasing MFPD of the nonwoven fabric given the same amount of LBEA present in the nonwoven fabric.

The nonwoven fabric, in accordance with certain embodiments of the invention, may comprise a basis weight from about 5 to about 100 grams-per-square-meter (gsm). The basis weight of the nonwoven fabric, according to certain embodiments of the invention, may comprise from about 5 to about 50 gsm. In certain embodiments of the invention, for example, the nonwoven fabric may comprise a basis weight from about 5 gsm to about 20 gsm. In accordance with certain embodiments the nonwoven fabric may comprise a basis weight from at least about any of the following: 5, 8, 10, 12, 15, and 20 gsm and/or at most about 100, 80, 75, 65, 50, 35, 25, and 20 gsm. Moreover, all whole number end points that can create a smaller range within a given range disclosed herein are within the scope of certain embodiments of the invention. By way of example, the foregoing disclosure of about 5 to about 100 gsm includes the disclosure of intermediate ranges, for example, of: from about 5 to about 99 microns; from about 5 to about 98 gsm; from about 5 to about 97 microns; etc.

In accordance with certain embodiments, the one or more LBEAs may also simultaneously act as an antistatic additive. For instance, the one or more LBEAs may provide anti-static properties to the nonwoven fabrics in addition to providing enhanced liquid barrier properties and/or imparting improved softness to the nonwoven fabric. Antistatic additives prevent or minimize the build-up of static charge, which may be particularly desirable for barrier fabrics used in medical fabrics, such as gowns and drapes, or for article in the protective apparel market. Accordingly, certain embodiments of the invention may beneficially and simultaneously impart improved softness, liquid barrier properties, and antistatic properties to the nonwoven fabric.

II. Articles Including a Barrier Nonwoven Fabric

In another aspect, the present invention provides articles including a nonwoven fabric including at least one LBEA as disclosed herein. In accordance with certain embodiments of the invention, the article may comprise a facemask, a surgical gown, a surgical drape, a lab coat, a filter, or an absorbent article. In accordance with certain embodiments of the invention, the article comprises an absorbent article, such as a diaper comprising at least one barrier leg cuff comprising a nonwoven fabric comprising at least one LBEA as disclosed herein. In accordance with certain embodiments of the invention, the barrier leg cuff may comprise a nonwoven including a LBEA as disclosed herein, either alone or laminated to an additional material such as an elastic nonwoven and/or an elastic film and/or an elastic tape or strand.

In accordance with certain embodiments of the invention, the article comprises a diaper including a front region, a back region, an intermediate crotch region located between the front region and the back region, and at least one barrier leg cuff (e.g., a pair of barrier leg cuffs). In accordance with certain embodiments of the invention, the barrier leg cuff may comprise a free distal edge and a contractible cuff (e.g., a gasketing cuff) disposed adjacent to a longitudinal edge of the diaper. The barrier leg cuff may be attached at least to the crotch region of the diaper.

Figure 3A:
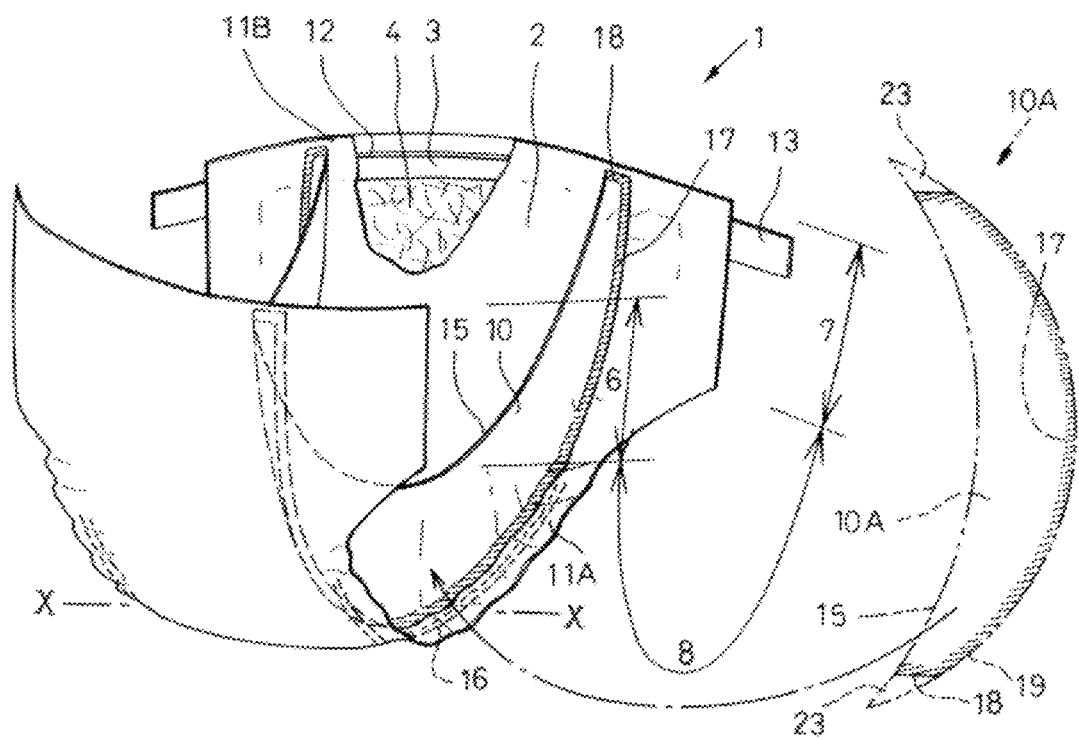
FIG. 3A illustrates a perspective view of an absorbent article according to one embodiment of the invention.
Figure 3B:
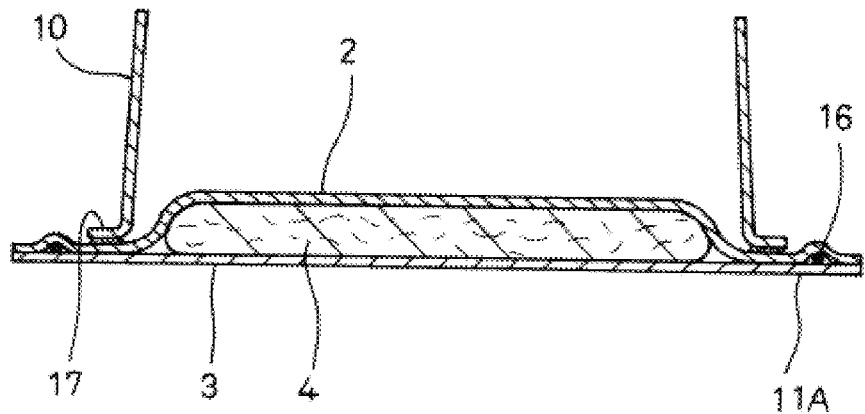
FIG. 3B illustrates a cross-sectional view taken along line X-X in of FIG. 3A.
Figure 3C:
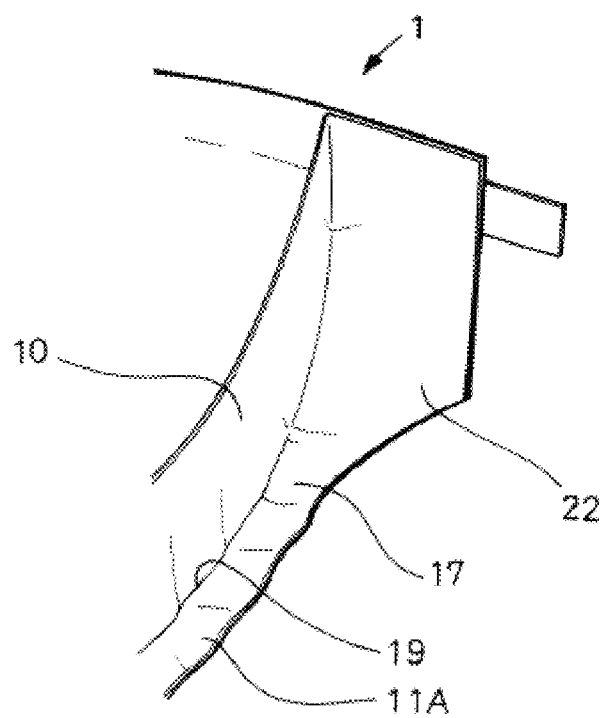
FIG. 3C illustrates a perspective view of a portion of the absorbent article of FIG. 3A.

FIGS. 3A through 3C illustrate an example absorbent article (e.g., a diaper) according to certain embodiments of the invention. In this regard, the embodiments illustrated in FIGS. 3A through 3C are merely illustrative and not limiting, such as with respect to any particular structure illustrated in FIGS. 3A through 3C. FIGS. 3A and 3B illustrate an example diaper 1 according to certain embodiments of the invention, in which the diaper 1 includes a liquid-permeable topsheet 2, a liquid-impermeable backsheet 3, and a liquid-absorbent core 4 sandwiched between the liquid-permeable topsheet 2 and the liquid-impermeable backsheet 3. The topsheet 2 and the backsheet 3 may outwardly extend from the periphery of the liquid-absorbent core 4 and may be bonded together in these outwardly extending regions to form leg surrounding flaps 11A and a waist surrounding flap 11B. The diaper 1 may be longitudinally composed of a front region 6, a rear region 7, and an intermediate crotch region 8 located between the front region 6 and the rear region 7. An elastic member (first elastic member) 12 may be bonded in its stretched state to, for example, the inner surface of the backsheet 3 circumferentially along the waist surrounding flap 11B of the rear region 7, and a pair of tape fasteners 13 may outwardly extend from transversely opposite side edges of the rear region 7, respectively. A pair of barrier leg cuffs 10 may longitudinally extend on the inner surface of the diaper 1 along transversely opposite (periphery) sides of the diaper 1 across the front and rear regions 6, 7 as well as the crotch region 8, in which the barrier leg cuffs 10 may bear against the wearer's crotch as the diaper 1 is worn. Each leg surrounding flap 11A may be cut away to form a circular-arc-shaped notch outside the associated barrier leg cuff 10 and an elastic member (second elastic member) 16 may be bonded in its stretched state to the inner surface of the backsheet 3 in parallel to and inside the circular arc or, parallel to the edge of the absorbent core.

Referring to FIG. 3B, the bonding margin 17 along which the barrier leg cuff 10 is bonded to the inner surface of the diaper 1 is dimensioned to be sufficiently large to cover the leg surrounding flap 11A as well as wings 22 of the front and rear regions 6, 7 and to define a substantially identical outline as that of the diaper 1.

Although FIGS. 3A through 3C illustrate a particular construction of an absorbent article according to one example embodiment of the invention, a wide range of other particular constructions incorporating a barrier nonwoven fabric as disclosed herein may be utilized. For example, certain embodiments of the invention may comprise an absorbent article as disclosed in U.S. Pat. No. 7,435,243 (disclosing an absorbent article comprising barrier leg cuffs and an elasticized outer leg cuff), in which the barrier leg cuffs may comprise a barrier nonwoven fabric as disclosed herein. The contents of U.S. Pat. No. 7,435,243 are incorporated by reference herein to the extent that such disclosure is consistent with the present disclosure. In accordance with certain embodiments of the invention, absorbent articles may comprise a wide-variety of structures including, by way of non-limiting examples, structures as described in any one of U.S. Pat. Nos. 4,738,677, 4,795,454, and 5,582,606, in which the barrier leg cuffs may comprise a barrier nonwoven fabric as disclosed herein. The contents of U.S. Pat. Nos. 4,738,677, 4,795,454, and 5,582,606 are each incorporated by reference herein to the extent that such disclosures are consistent with the present disclosure.

III. Methods of Producing a Barrier Nonwoven Fabric

In yet another aspect, the invention provides a method of forming a barrier nonwoven fabric according to embodiments disclosed herein and disclosed throughout the present disclosure. In accordance with certain embodiments of the invention, the method of forming a nonwoven fabric may comprise a step of forming a polymer melt comprising a LBEA comprising an amide (as discussed throughout) and forming one or more nonwoven layers from the polymer melt to provide the nonwoven fabric. In accordance with certain embodiments, the method may also comprise meltspinning the polymer melt to form a plurality of meltspun filaments.

In accordance with certain embodiments of the invention, the method of forming a barrier nonwoven fabric as disclosed herein may comprise providing or forming a carded nonwoven web containing staple fibers, in which the staple fibers comprise one or more LBEA as discussed previously. In this regard, embodiments according to certain embodiments of the invention may comprise providing and/or forming one or more meltspun nonwoven layer and/or providing and/or forming one or more staple fiber-containing nonwoven layers and combining them to form a barrier nonwoven fabric, in which one or more of the nonwoven layers may comprise one or more LBEA.

In accordance with certain embodiments of the invention, the one or more LBEA may be added to the polymer melt used to form the plurality of fibers of one or more nonwoven layers. Additionally or alternatively, the one or more LBEAs may be topically applied to one or more nonwoven layers of the nonwoven fabric. In accordance with certain embodiments of the invention and as provided above, the LBEA may comprise an amide. The LBEA, in accordance with certain embodiments of the invention, may comprise a primary amide, a secondary amide, a tertiary amide, a bis-amide, or any combination thereof. In accordance with certain embodiments of the invention, the one or more LBEAs may comprise one or more primary amides. By way of example, primary amides suitable as an LBEA in accordance with certain embodiments of the invention comprise erucamide, oleamide, strearamide, behenamide, or any combination thereof. Alternatively or additionally, certain embodiments of the invention may comprise one or more LBEAs comprising one or more secondary amides. By way of example, secondary amides suitable as an LBEA in accordance with certain embodiments of the invention comprise oleyl palmitamide, strearyl erucamide, or any combination thereof. Alternatively or additionally, certain embodiments of the invention may comprise one or more LBEAs comprising one or more bis-amides, such as ethylene bis-amides. By way of example, bis-amides suitable as an LBEA in accordance with certain embodiments of the invention comprise ethylene bis-strearamide, ethylene bis-oleamide, or any combination thereof.

In this regard, methods according to certain embodiments of the invention may comprise adding, either via the polymeric melt used to extrude at least some of the fibers of the nonwoven fabric and/or via a topical application, one or more LBEAs from about 0.05% by weight of the fibers to about 10% by weight of the fibers (e.g., 0.05 to 8% by weight of the fibers, 0.05 to 6% by weight of the fibers, etc.). In accordance with certain embodiments of the invention, the plurality of fibers forming an individual nonwoven layer may comprise one or more LBEAs from at least about any of the following: 0.05%, 0.08%, 1.0%, 1.5%, 2.0%, 2.5%, and 3.0% by weight of the fibers and/or at most about 10%, 8%, 6%, 5%, 4%, and 3% by weight of the fibers (e.g., about 1-3% by weight of the fibers, about 2-5% by weight of the fibers, etc.). Moreover, all whole number end points and/or single decimal (e.g., numbers reported to the nearest tenth) end points that can create a smaller range within a given range disclosed herein are within the scope of certain embodiments of the invention. By way of example, the foregoing disclosure of about 1 to about 10% by weight of the fibers includes the disclosure of intermediate ranges, for example, of: from about 1 to about 2% by weight of the fibers; from about 1 to about 2.5% by weight of the fibers;

from about 1 to about 3% by weight of the fibers; etc. In this regard, any layer or layers comprising a LBEA may independently comprise a weight percentage of one or more LBEAs according to any of the foregoing ranges.

In accordance with certain embodiments of the invention, the method may comprise a step of consolidation or bonding the one or more nonwoven layers for form a unitary and/or cohesive nonwoven fabric exhibiting enhanced barrier properties. The bonding step, for example, may comprise a thermal bonding operation, a mechanical bonding operation, an adhesive bonding operation, or any combination thereof. In accordance with certain embodiments of the invention, the bonding of the nonwoven fabric may comprise thermal bonding with a calendar, ultrasonic bonding system, or hot fluid (e.g. through-air bonding). Mechanical bonding, in accordance with certain embodiments, may comprise mechanical entanglement of fibers by different methods, such as needle-felting or hydro-entanglement.

Figure 4:
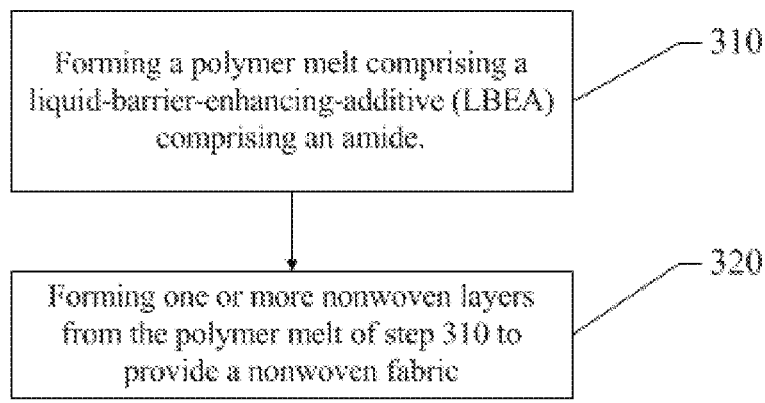
FIG. 4 illustrates a process flow diagram for forming a nonwoven fabric according to an embodiment of the invention.

As shown in FIG. 4, methods of forming a barrier nonwoven fabric, in accordance with certain embodiments of the invention, may comprise steps of forming a polymer melt comprising a LBEA comprising an amide (as disclosed throughout the present disclosure) at operation 310 and forming one or more nonwoven layers from the polymer melt of step 310 to provide a nonwoven fabric at operation 320. Although not shown in FIG. 4, the nonwoven fabric may be subsequently consolidated or bonded as discussed above.

As noted previously, the barrier-enhancing impact of one or more LBEA, according to certain embodiments of the invention, may be greater for smaller diameter fibers (e.g., fine meltblown fibers) than for larger fiber diameters of the same construction. In certain embodiments of the invention, for example, a larger LSTST value for a meltblown nonwoven layer formed from a reduced production throughput may be realized as compared to a comparative meltblown nonwoven layer formed from the same material, but formed at a larger or faster throughput. For instance, meltblown fibers made at lower throughputs may generally comprise smaller average diameters than if formed at a higher throughput. In accordance with certain embodiments of the invention, a larger increase in liquid barrier properties (e.g., LSTST) may be realized in smaller diameter fibers as compared to larger diameter fibers formed from the same process (e.g., meltblowing process), in which all fibers comprise the same amount of LBEA. In this regard, methods according to certain embodiments of the invention may comprise forming one or more meltblown nonwoven layers comprising fine fibers (e.g., from about 0.5 microns to about 4 microns or as generally discussed above) including one or more LBEAs, in which the one or more meltblown nonwoven layers including a LBEA is formed at a production speed (e.g., throughput) of below about 1000 meters-per-minute (MPM) (e.g., less than 700 MPM). In accordance with certain embodiments of the invention, method may comprise forming one or more meltblown nonwoven layers comprising fine fibers (e.g., from about 0.5 microns to about 4 microns or as generally discussed above) including one or more LBEAs, in which the one or more meltblown nonwoven layers including a LBEA is formed at a production speed (e.g., throughput) from at least about any of the following: 200, 300, 400, 500, 600, and 700 MPM and/or at most about 1200, 1100, 1000, 900, 800, and 700 MPM. Such a meltblown nonwoven web may be provided as a stand-alone layer, combined with a reinforcement layer, or incorporated into a multilayer nonwoven fabric (composite) as disclosed in the present disclosure.

IV. Working Examples

The present disclosure is further illustrated by the following examples, which in no way should be construed as being limiting. That is, the specific features described in the following examples are merely illustrative and not limiting.

A. Description of Test Methods

Basis Weight: The basis weight of the following examples was measured in a way that is consistent with ASTM D756 and EDANA ERT-40,3-90 test methods. The results were provided in units of mass per unit area in grams-per-square-meter (gsm) and were obtained by weighing a minimum of ten individual samples having a size of 10 cm by 10 cm. The basis weights for each of the Comparative Examples and Examples below were obtained in this manner.

Air Permeability: Air permeability data was produced using a Tex-Test FX3300 Air Permeability Tester manufactured by Tex-Test AG of Zurich, Switzerland. The Tex-Test FX3300 Air Permeability Tester was used in accordance with the manufacturer's instructions using a 38 mm orifice and a pressure drop of 125 Pa as per ASTM D-737 test method. Readings were made on single ply or layer and the results were recorded in the units of $m^3$/m/min or m/min.

Low Surface Tension Strike Through (LSTST): The Low Surface Tension Strike Through method utilized was based on EDANA test method WSP70.3(05) with a few modifications. A first modification to the EDANA test method WSP70.3(05) was that a low surface tension fluid, described below in more detail, was utilized instead of a simulated urine solution of a 9 g/liter solution of sodium chloride in distilled water having a surface tension of 70±2 mN/m. A second modification was that for the both the Comparative Examples and the Examples, the measurement was performed on a double ply or two (2) layers of the sample. A third modification to the EDANA test method WSP70.3(05) was that Ahlstrom Filtration filter paper code #989 (available from Empirical Manufacturing, Inc., 7616 Reinhold Drive, Cincinnati, Ohio 45237, USA) having dimensions of 4 inches by 4 inches was used as a blotter or absorbent paper positioned under the sample, instead of the suggested blotter paper ERT FF2, which is available from Hollingsworth & Vose Co. or East Walpole, Mass. The five blotter papers used per test were stacked with the rougher surface facing the incoming fluid.

The low surface tension liquid utilized in the EDANA test method WSP70.3(05) was prepared as follows: in a clear clean flask, 500 ml distilled water was provided and 2.100 grams of a nonionic surfactant, which is available under the trademark Triton® X-100 from Sigma-Aldrich of St. Louis, Mo., was added to the flask containing the 500 ml distilled water. Thereafter, distilled water in an amount of 5,000 ml was added to the same flask. The distilled water and non-ionic surfactant solution was mixed for a minimum of 30 minutes. The surface tension of the solution was measured, to ensure it was between 31 mN/m and 32.5 mN/m, and preferably about 32 mN/m, to qualify as a low surface tension liquid. The surface tension of the solution was determined by method D1331-56 ("Standard test method for surface and interfacial tension solution of surface active agents") using a Kriiss Kl 1 MK1 tensiometer.

For the purposes herein, the LST ST-Time is defined as the strike through time in seconds measured by this method.

Fiber Dimension and Denier: Fiber dimensions for the continuous spunbond filaments were measured on specimens that were first frozen and cut while still cold with a fine razor blade; this is important to avoid deformation of the filament cross section for those that are made from polymers that are too ductile at room temperature (e.g., above their glass transition). Those specimens were then mounted in a way that the cross section of the filaments can be observed and measured using a scanning electron microscope. Those measurements are made using the measuring tools provided with the software of the microscope and calibrated as per the operating procedure (e.g., using a standard sample with targets of known dimensions). For the filaments having a round cross section, the diameter of the filaments was measured. For the filaments having a ribbon shape cross section, the width or longest dimension was measured. For round filaments the diameter and the estimated density of polypropylene were used to calculate their denier, the latter being the weight in grams of a 9000 l.m. filament. For the filaments having a ribbon shaped cross-section, the denier was calculated based on the maximum width measured, the density of the polymer, and the assumption that the ratio of width to thickness is 3:1. The latter is a constant used for that spinneret and was arrived at based on measurement done in the past over a range of throughputs. A different spinneret design would likely give a different ratio. Each result reported was the average of measurements made on 10 fibers.

Pore Size Distribution: The pore size distributions of the Comparative Examples and Examples were measured using a capillary flow parameter. A typical instrument to perform this test is the PMI Capillary Flow Parameter model CFP-1200-ACL-E-X-DR-2S, available from Porous Materials, Inc. of Ithaca, N.Y. For this test, the wetting fluid used had a surface tension of 15.9 mN/m and is available under the trademark Galwick® from Porous Materials, Inc.

The method used to measure the cumulative flow and pore size distribution was provided by the equipment manufacturer and is identified as "Capillary Flow Porometry Test" using the "Wet up/Dry up" mode. A wrinkle free, clean circular sample is obtained from the Comparative Examples and Examples having a diameter of about 1.0 cm. The sample was saturated with the wetting fluid and then mounted into the cell of the PMI Capillary Flow Parameter, as per the manufacturer's instruction. When the mounting was complete, the apparatus was run by the apparatus software in the "Wet up/Dry up" mode to first record a flow vs. pressure curve for the sample saturated with the wetting fluid. When the flow v. pressure curve is recorded for the saturated sample, and the fluid has been expulsed from the pores, a flow vs. pressure curve was measured a second time on the same sample mounted in the instrument. The data generated includes the mean flow pore diameter or "MFPD," where the pore size was calculated from the pressure where the half-dry curve intersects with the wet curve. The mean flow pore diameter was such that 50% of the flow is through pores larger than the mean flow pore.

Coefficient of Friction Method: Coefficient of friction was measured as per ASTM D1894 for a nonwoven sample against itself. The results reported were for measurements made with the sample being pulled along the machine direction of the nonwoven. The tests were performed using IMASS Slip/Peel Tester Model SP-2000 made by IMASS Inc., Accord, MA, USA.

Hydrohead Test Method: Hydrohead measurements were performed using the AATCC 127 method and a pressure increase rate of 20 mBar/min.

B. Comparative Examples, Examples, and Results for Multilayer Nonwovens

Figure 6:
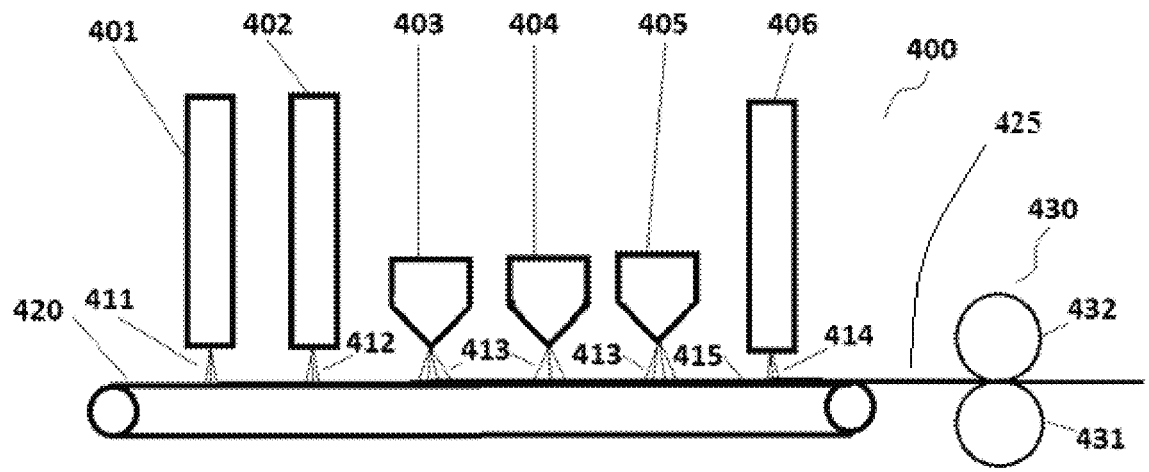
FIG. 6 shows an operational schematic illustrating a method for making a nonwoven fabric according to certain embodiments of the invention.

Comparative Examples 1 to 4 and Examples 1 to 4 were made on a line fitted with six production beams (e.g., first, second, third, fourth, fifth, and sixth production beams, respectively) designed by Reifenhauser Reicofil GmbH & Co. KG of Troisdorf, Germany, which is illustrated as process 400 in FIG. 6. The first production beam 401 and second production beam 402 formed continuous filaments 411, 412, respectively. Continuous filaments 411, 412 were deposited on a moving belt 420. The third production beam 403, the fourth production beam 404, and the fifth production beam 405 each formed meltblown fibers 413 that were in turn laid on top of the moving web. Subsequently, the sixth production beam 406 formed continuous filaments 414 that were laid on top of the composite layer 415. In all Comparative Examples and Examples, the fine fiber meltblown layers 413 from the third, fourth, and fifth production beams 403, 404, 405 collectively account for a basis weight of approximately 18% by weight of the total composite basis weight.

The resulting composite web 425 was bonded together using a calendar 430 fitted with a smooth roll 431 and an embossed roll 432. The embossed roll pattern is identified under the commercial code U2888 from A+E Ungricht GMBH & Co. KG of Monchengladbach, Germany. The U2888 pattern is described as being formed from a plurality of raised pins with a surface contact area or "land" area covering at least about 16% and no greater than about 20% of the total area of the embossed portion of the roll containing pattern and having a pin density of about 50 pins/$cm^2$.

In each of Comparative Examples 1 to 4 and Examples 1 to 4, the spunbond fibers formed by the first production beam 401, the second production beam 402, and the sixth production beam 406 were extruded from a polypropylene resin having a melt flow rate ("MFR") of 30 g/10 min., available under the tradename Isplen PP089Y1E from Repsol, of Madrid, Spain. Also, the meltblown fibers formed by the third, fourth, and fifth production meltblown beams 403, 404, 405 were extruded from a polypropylene resin having a meltflow rate ("MFR") of 1200 g/10 min, available under the tradename HL712FB available from Borealis of Vienna, Austria.

Comparative Example 1 (C1)

This nonwoven sample was produced on the above described production beams at a speed of 693 meters/min, wherein the first production beam 401, the second production beam 402, and the sixth production beam 406 had spinnerets with capillaries having a round cross-sectional geometry, as indicated above. The resulting S/S/M/M/M/S layers were then bonded using the embossed roller with pattern U2888. The resulting fabric included two round-shaped spunbond layers, three meltblown layers, and a final round-shaped spunbond layer, wherein the spunbond layers have fibers with a round cross-sectional geometry and an aspect ratio of less than 1.5 (e.g., 1.0 to less than 1.5). The meltblown layers of Comparative Example 1 were formed from the third, fourth, and fifth production beams. Meltblown fibers formed by these beams were extruded from a polypropylene resin having a MFR of 1200 g/10 min. Total basis weight measurements and basis weight calculations per layer are provided in Table 1.

Example 1

This nonwoven was produced in the same manner as Comparative Example 1 with the exception of the addition of additive masterbatch (e.g., LBEA masterbatch) that accounted for 3% by weight of the composition being fed to the first production beam 401, the second production beam 402, and the sixth production beam 406. The masterbatch (e.g., LBEA masterbatch) consisted principally of 30% by weight of erucamide dispersed into a polyolefin resin. Example 1 had similar construction as Comparative Example 1 in regard to basis weight targeted per layer and for the composite.

Comparative Example 2 (C2)

This nonwoven sample was produced in the same manner as Comparative Example 1 with the exception that the first production beam 401 and the sixth production beam 406 beams were operating with ribbon shaped spunbond fibers. The total basis weight measurement and basis weight calculations per layer for Comparative Example 2 (C2) are reproduced below in Table 1.

Example 2

This nonwoven sample was produced in the same manner as Comparative Example 2 with the exception that the additive masterbatch (e.g., LBEA masterbatch) described in Example 1 was added at a rate of 3% by weight to the formulation fed to the first production beam 401, the second production beam 402, and the sixth production beam 406.

Comparative Example 3 (C3)

This nonwoven sample was produced in the same manner as Comparative Example 2 with the exception that the fifth production beam 405 was not operated, resulting in a configuration of RSMMR, and the throughputs of the third production beam 403 and the fourth production beam 404 were increased to produce about the same overall content in meltblown fibers.

Example 3

This nonwoven sample was produced in the same manner as Comparative Example 3 with the exception that the additive masterbatch (e.g., LBEA masterbatch) described in Example 1 was added at a rate of 3% by weight to the formulation fed to the first production beam 401, the second production beam 402, and the sixth production beam 406.

Comparative Example 4 (C4)

This nonwoven was produced in the same manner as Comparative Example 3 with the exception that speed was increased to 808 meters/min, and the throughput of each beam was increased to keep the basis weight of each layer as well as the overall basis weight the same.

Example 4

This nonwoven sample was produced in the same manner as Comparative Example 4 with the exception that the additive masterbatch (e.g., LBEA masterbatch) described in Example 1 was added at a rate of 3% by weight to the formulation fed to the first production beam 401, the second production beam 402, and the sixth production beam 406.

TABLE 1

|  | | Basis weights estimated from thruput process settings | | |
|---|---|---|---|---|
| | Total Measured basis weight (gsm) | Beam 1 (gsm) | Beam 2 (gsm) | sum of Beams 3, 4, 5 (gsm) | Beam 6 (gsm) |
| Comparative 1 (C1) | 13.4 | 3.7 | 3.7 | 2.4 | 3.7 |
| Example 1 (1) | 13.5 | 3.7 | 3.7 | 2.5 | 3.7 |
| Comparative 2 (C2) | 13.7 | 3.7 | 3.7 | 2.5 | 3.7 |
| Example 2 (2) | 13.9 | 3.8 | 3.8 | 2.5 | 3.8 |
| Comparative 3 (C3) | 14.3 | 3.9 | 3.9 | 2.6 | 3.9 |
| Example 3 (3) | 14.81 | 4.0 | 4.0 | 2.7 | 4.0 |
| Comparative 4 (C4) | 13.95 | 3.8 | 3.8 | 2.5 | 3.8 |
| Example 4 (4) | 13.54 | 3.7 | 3.7 | 2.5 | 3.7 |

The physical properties as measured for all Comparative examples (C1-C4) and the Examples (1-4), in accordance with certain embodiments of the invention, are included in Table 2 provided below.

TABLE 2

| example # | Production speed - MPM | Basis Weight (gsm) | MFPD [micron] | Airpermeability [m/min] | LSTST[sec] | Hydrohead (mbar) | continuous round filament fiber avg. diameter (microns) | Continuous ribbon filaments avg. widest dimension (width) (microns) | Meltblown avg. fiber diameter (microns) | Average coefficient of Iridion |
|---|---|---|---|---|---|---|---|---|---|---|
| C1 | 697 | 13.4 | 11.6 | 44.7 | 12.7 | 25.1 | 15.7 | | 1.9 | 0.55 |
| 1 | 697 | 13.5 | 12.3 | 40.8 | 14.4 | 24.7 | 14.5 | | 1.9 | 0.24 |
| C2 | 697 | 13.7 | 12.2 | 39.7 | 13.1 | 24.1 | 15.1 | | 1.9 | 0.76 |
| 2 | 697 | 13.9 | 12.0 | 34.3 | 19.8 | 24.2 | 15.1 | 28.3 | 1.9 | 0.33 |
| C3 | 697 | 14.3 | 17.5 | 53.5 | 10.6 | 15.7 | 15.4 | 28.3 | 2 | 0.61 |
| 3 | 697 | 14.8 | 16.5 | 53.1 | 14.1 | 16.2 | 15.4 | 27.5 | 2 | 0.29 |
| C4 | 808 | 14.0 | 20.0 | 65.7 | 8.4 | 16.2 | 16.2 | 29.1 | 2.1 | 0.60 |
| 4 | 808 | 13.5 | 19.6 | 66.8 | 11.4 | 12.0 | 16.6 | 32.4 | 2.1 | 0.31 |

Figure 5:
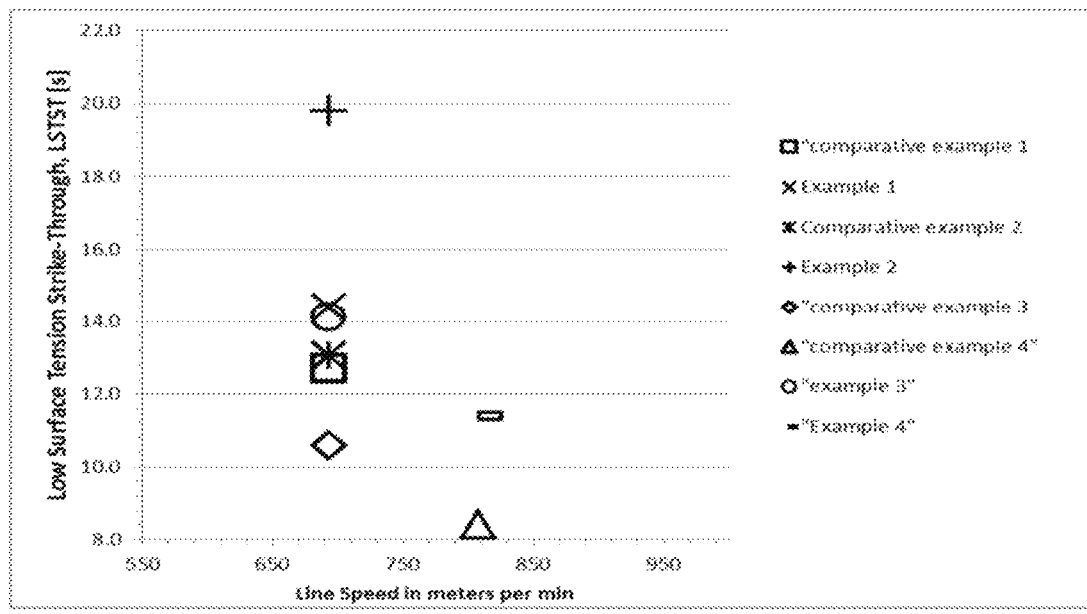
FIG. 5 shows a plot of LSTST for Example and Comparative nonwoven fabrics.

FIG. 5 provides a graph of the LSTST for each of Comparative Examples 1-4 and Examples 1-4. As shown in FIG. 5, the LSTST value for each of Examples 1-4 is larger than Comparative Examples 1-4, respectively. FIG. 5 also illustrates that the same amount of LBEA additive to non-round cross-sectional fibers (e.g., Example 2) provides a significantly greater increase in LSTST than to round cross-sectional fibers. In this regard, the impact of the LBEA provided a notable improvement in LSTST for all Examples according to certain embodiments of the invention, but the magnitude of improvement in LSTST is surprisingly larger for non-round cross-sectional fibers. FIG. 5 also illustrates that the magnitude of improvement in LSTST is surprisingly larger for the multilayer nonwoven fabrics (e.g., nonwoven composites) having a natural structure having a lower air permeability and/or MFPD. For instance, nonwoven fabrics having a naturally lower MFPD due, for example, to operating parameters and/or construction, realize a notably larger magnitude of LSTST improvement with the same amount of LBEA additive.

C. Meltblown Nonwovens

Additional trials were conducted following the above working examples to determine the functionality of incrementally adding the same additives into meltblown layers, to illustrate the further improvement in LSTST in a composite structure, such as the composite structures used above (i.e., SSMMMS or RSMMR). This was executed by production of stand-alone meltblown layers as described below, then tested by utilizing the same LSTST solution (32 dyne) in a single droplet to compare the amount of time between droplet contact with the meltblown surface and penetration into the meltblown substrate.

Comparative meltblown examples were produced using a meltblown beam designed by Reifenhauser Reicofil GmbH & Co. KG of Troisdorf, Germany with 35 hpi (Holes per inch) spinpack on a 1 Meter commercial die. The commercial grade meltblown resin from Total 3962 was used for the production of the meltblown layer. For this experiment the throughputs, process conditions, and additive rates are shown in Table 3 below.

Comparative Sample 5 (C5)

For Comparative Sample 5 the meltblown resin described above was fed to the system and meltblown fibers were blown and collected on a carrier fabric that was laid on top of a moving collection belt. That carrier fabric consisted of a bonded spunbond nonwoven having a basis weight of 17 gsm and made of polypropylene.

Sample 5

Sample 5 was made in a similar manner as Comparative Sample 5 with the exception of the addition of additive masterbatch (e.g. LBEA masterbatch) that accounted for 6% by weight of the composition being fed to this meltblown beam. The masterbatch (e.g. LBEA masterbatch) consisted principally of 30% by weight of erucamide dispersed into a polyolefin resin.

Comparative Sample 6 (C6)

This Comparative Sample 6 was made in a manner similar to Comparative Sample 5 with the exception that a higher throughput was used.

Sample 6

Sample 6 was made in a manner similar to Sample 5 with the exception that the throughput was also increased similarly to that of Comparative Sample 6.

Sample 7

Sample 7 was made in the same manner as Sample 5 with the exception that only 3% by weight of the additive masterbatch (LBEA masterbatch) was added to the composition being fed to the meltblown beam.

Sample 8

Sample 8 was made in the same manner as sample 6 with the exception that only 3% by weight of the additive masterbatch (LBEA masterbatch) was added to the composition being fed to the meltblown beam.

The above Comparative Example 5 and Example 5 were subjected to the following testing procedure: A single layer of the meltblown collected on the carrier web was used with the meltblown facing toward the top and a single droplet of the LSTST fluid was deposited on the top surface (i.e., directly onto the meltblown). The time interval between when the droplet was deposited and when it was absorbed was recorded and is reported as Droplet Penetration Time. Each piece of sample was used only once. Results can be found in Table 3. In this regard, a longer time to achieve or realize penetration is correlated with improved LSTST values. Additionally, the LSTST testing was performed on Comparative Samples 5 and 6 as well as the Samples 5, 6, 7 and 8 as described above for the multilayer (e.g., nonwoven composites) testing for LSTST values. The results of these tests are also provided below in Table 3.

TABLE 3

| SID | RPM | T/P [kg/h/m] | t/p [ghm] | LS [mpm] | DCD | Additive % | BW [gsm] | LSTST [sec] | Droplet Penetration Time [sec] |
|---|---|---|---|---|---|---|---|---|---|
| Comparative example 5 | 57.2 | 29.3 | 0.30 | 61 | 6 | 0 | 8 | 39.1 | 1.75 |
| Comparative example 6 | 114.4 | 58.5 | 0.60 | 98 | 6 | 0 | 9 | 30.3 | |
| Example 5 | 57.2 | 29.3 | 0.30 | 49 | 6 | 6 | 9 | 64.7 | 3.03 |
| Example 6 | 114.4 | 58.5 | 0.60 | 81 | 6 | 6 | 11 | 39.6 | |
| Example 7 | 57.2 | 29.3 | 0.30 | 41 | 6 | 3 | 13 | 80.4 | |
| Example 8 | 114.4 | 58.5 | 0.60 | 94 | 6 | 3 | 10 | 49.3 | |

In Table 3, SID=sample identification number;
RPM=pump speed in revolution per minute (RPM);
T/P [kg/h/m]=polymer throughput in kg/hour/meter of die width;
t/p [ghm]=polymer throughput per capillary in gram/hole/min (calculated);
LS=collection belt speed in meters/min;
Est. BW=Estimated basis weight using kg/h/m vs collection belt speed (e.g. at TP of 29.3 kg/h/m, LS of 61 m/min we get=(29.3 kg/hr/m×1000 g/kg/60 min/hr)/61 m/min=8 grams/square meter); and
DCD=Die to collector distance—the Meltblown die tip distance to collection belt measured in inches.

Figure 7:
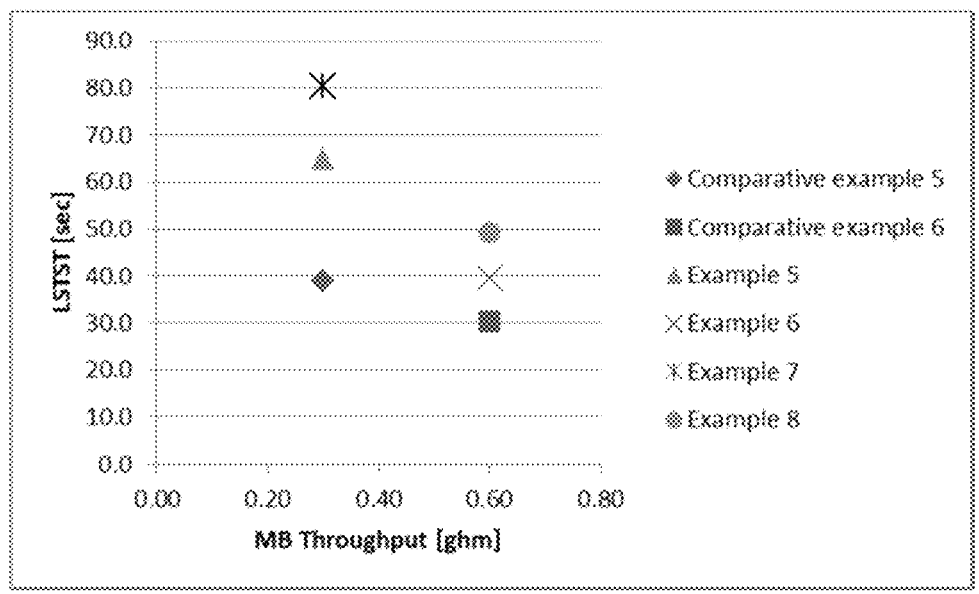
FIG. 7 shows a plot of LSTST for certain Example and Comparative nonwoven fabrics.

The increase in droplet penetration time on the sample containing the LBEA, as illustrated in Example 5 in Table 3, as well as the improved LSTST values are indicative of improved resistance to penetration, and should result in a composite structure with additional improved performance. The results from Table 3, for instance, can be seen as an indication that the presence of a LBEA added to all layers of a multilayer nonwoven fabric (composite), or added only in one or more interior meltblown layers of a multilayer nonwoven fabric (composite), or as a stand-alone meltblown layer will provide improved liquid barrier resistance. The LSTST results are illustrated in Table 3 and are graphically illustrated in FIG. 7.

D. Spunbond Nonwovens

Additional trials were conducted following the above working examples, in which three different LBEAs were utilized. For these additional trails, the LBEAs selected were behenamide (LBEA-1), ethylene bis-oleamide (LBEA-2), and erucamide (LBEA-3). These LBEAs where added to a polypropylene spunmelt nonwoven as discussed in more detail below. For this example, for instance, the LBEAs were added to formulations used to produce single layer spunbond nonwovens on a pilot line. The assumption is that a significant impact on LSTST from a LBEA in such construction should also translate into similar effect for multilayer nonwovens or when added to a meltblown layer.

Figure 8:
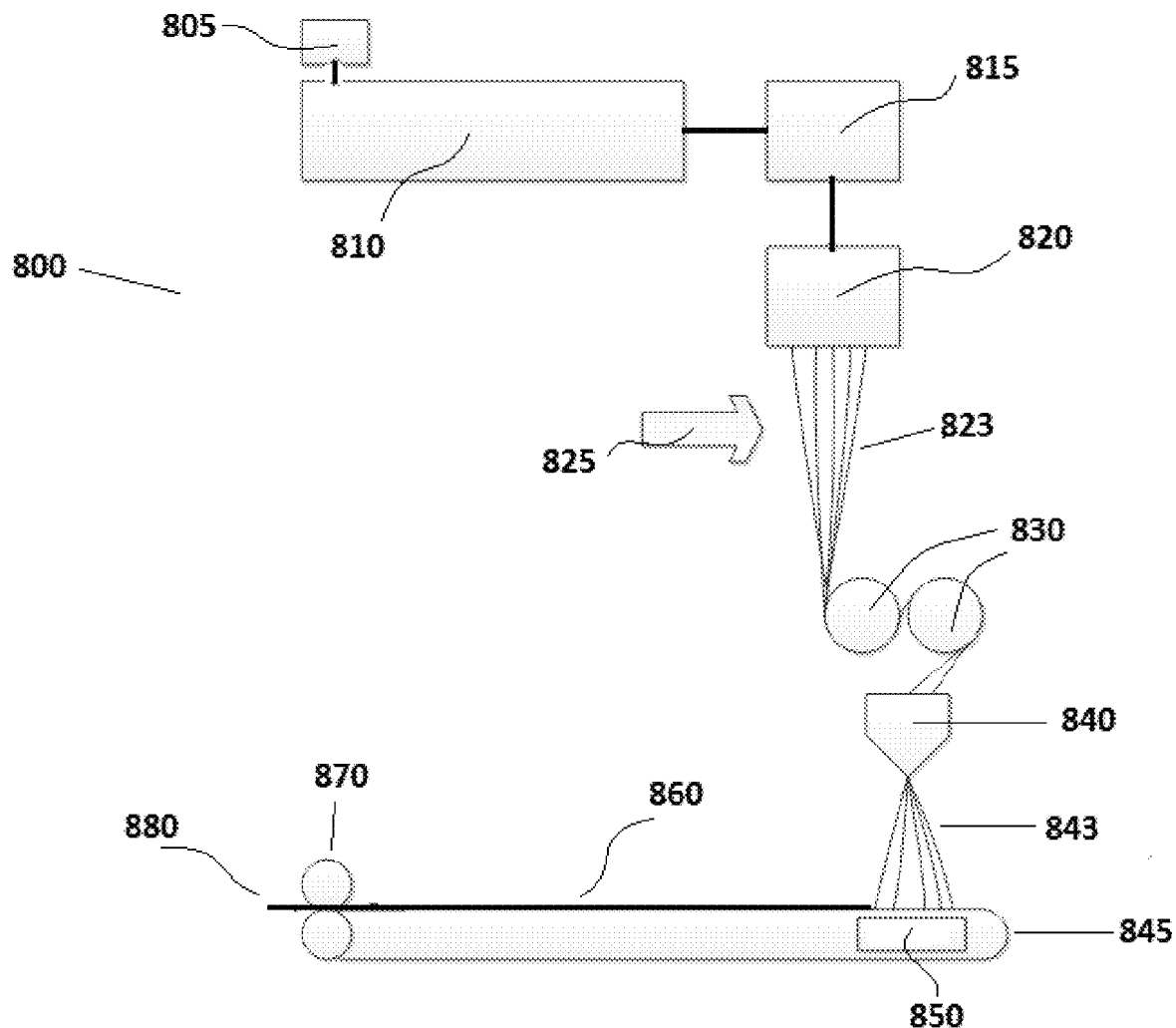
FIG. 8 shows a schematic of the pilot line used to prepare single layer spunbond nonwovens for certain examples and comparative examples.

Examples and comparative examples were made on a pilot line where the respective formulations were melted and extruded through a spinneret having a multitude of capillaries forming filaments from the molten polymer. The filaments were air quenched and drawn by using rolls for which the rotational speed was controlled. At the exit of the rolls, the filaments were blown toward and deposited on a moving surface to form a web. This web was carried to a calendar where the web was bonded by passing the web between a heated metal roll with a smooth surface and another metal roll with a surface having raised patterns that form the bonding points. FIG. 8 provides a schematic of the pilot line 800. The pilot line 800 includes a feed system or blender 805 for loading polymeric material into extrusion system 810 to provide molten polymer. The molten polymer exits the extrusion system 810 and is pumped (and optionally filtered) at operation 815 prior to being forced through spinneret 820, which includes several capillaries through which the molten polymer is forced to form molten filaments 823 exiting the spinneret. The molten filaments 823 exiting the spinneret 820 are subjected to quench air 825 and are drawn by rotating draw rolls 830. After exiting the rotating draw rolls 830, the drawn filaments 843 are blown at operation 840 toward and deposited on a travelling collection belt 845. As shown in FIG. 8, a vacuum box 850 may be utilized to facilitate deposition of the drawn filaments 843 onto the travelling collection belt 845 to form a nonwoven web 860. The nonwoven web 860 is then passed through a calendar 870 to bond the nonwoven web to provide a single layer spunbond nonwoven 880. This pilot line produced a more compacted spunbond than typically achieved on commercial line; however, it was consider suitable as it was used to compare different formulations.

For this experiment the spinneret selected had 240 capillaries forming filaments. These capillaries had a round cross section and had an exit diameter of about 0.38 mm.

For all examples and comparative examples, the polymer used as matrix was 34 MFR polypropylene known as CP360H available from Braskem America Inc., 1735 Market Street, Philadelphia Pa.

A throughput of 0.51 gram per hole per minutes (ghm) was targeted for all trials. To obtain samples of different basis weight, the speed of the collection belt was changed while maintaining the polymer throughput through the spinneret.

For all the examples of spunbond fabrics, the LBEAs were introduced as a masterbatch concentrate made by melt dispersing 20% by weight of the LBEA in a suitable polymer matrix consisting mainly of polypropylene.

One of the LBEAs selected was behenamide (LBEA-1), a primary amide additive having a greater resistance to thermal degradation or volatilization than erucamide. This resistance is typically characterized by identifying the temperature at which during thermogravimetric analysis (TGA) the chemical begins to lose weight rapidly, suggesting breakdown into volatile by-products or simply volatilization of the chemical. The other LBEA selected was ethylene bis-oleamide (LBEA-2), a bis-amide that also has a higher thermal degradation resistance than erucamide Comparative Example 7 (C7)

This nonwoven was produced on the pilot line described above extruding CP360H polypropylene polymer characterized as 34 MFR homopolymer at a throughput of 0.51 ghm. For this sample the belt speed was set to produce a basis weight of about 25 gsm.

Example 9 (E9)

This nonwoven sample was produced on the pilot line described above using a throughput of 0.51 ghm with a blend of CP360H polypropylene and a behenamide masterbatch mixed in proportions selected to produce a 2000 ppm concentration (e.g., 0.2% by weight) of this LBEA in the formulation fed to the extruder of the pilot line. The belt speed was set to produce a basis weight of about 25 gsm for this sample.

Example 10 (E10)

This sample was produced in a similar way to Example 9 with the exception that enough behenamide masterbatch was added to achieve a 4000 ppm concentration (e.g., 0.4% by weight) of this LBEA.

Example 11 (E11)

This sample was produced in a similar way to Example 9 with the exception that enough behenamide masterbatch was added to achieve a 9000 ppm concentration (e.g., 0.9% by weight) of this LBEA.

Example 12 (E12)

This nonwoven was produced on the above pilot line using a throughput of 0.51 ghm with a blend of CP360H polypropylene polymer and an ethylene bis-oleamide masterbatch mixed in proportions selected to produce a 2000 ppm concentration (e.g., 0.2% by weight) of this LBEA in the formulation fed to the extruder of the pilot line. The belt speed was set to produce a basis weight of about 25 gsm for this sample.

Example 13 (E13)

This sample was produced in a similar way to Example 12 with the exception that enough ethylene bis-oleamide masterbatch was added to achieve a 4000 ppm concentration (e.g., 0.4% by weight) of this LBEA.

Example 14 (E14)

This sample was produced in a similar way to Example 12 with the exception that enough ethylene bis-oleamide masterbatch was added to achieve a 9000 ppm concentration (e.g., 0.9% by weight) of this LBEA.

Comparative Example 8 (C8)

This nonwoven was produced on the above pilot line using CP360H polypropylene polymer at a throughput of 0.51 ghm. The belt speed was set to produce a basis weight of about 45 gsm for this sample.

Example 15 (E15)

This nonwoven was produced on the above pilot line using a throughput of 0.51 ghm using a blend of CP360H polypropylene polymer and a behenamide masterbatch mixed in proportions selected to get a 2000 ppm concentration (e.g., 0.2% by weight) of this LBEA in the formulation fed to the extruder of the pilot line. The belt speed was set to produce a basis weight of about 45 gsm for this sample.

Example 16 (E16)

This sample was produced in a similar way to Example 15 with the exception that enough behenamide masterbatch was added to achieve a 4000 ppm concentration (e.g., 0.4% by weight) of this LBEA.

Example 17 (E17)

This sample was produced in a similar way to Example 15 with the exception that enough behenamide masterbatch was added to achieve a 9000 ppm concentration (e.g., 0.9% by weight) of this LBEA.

Example 18 (E18)

This nonwoven was produced on the above pilot line using a throughput of 0.51 ghm using a blend of CP360H polypropylene polymer and an ethylene bis-oleamide masterbatch mixed in proportions selected to have a 2000 ppm concentration (e.g., 0.2% by weight) of this LBEA for the formulation fed to the extruder of the pilot line. The belt speed was set to produce a basis weight of about 45 gsm for this sample.

Example 19 (E19)

This sample was produced in a similar way to Example 18 with the exception that enough ethylene bis-oleamide masterbatch was added to achieve a 4000 ppm concentration (e.g., 0.4% by weight) of this LBEA.

Example 20 (E20)

This sample was produced in a similar way to Example 18 with the exception that enough ethylene bis-oleamide masterbatch was added to achieve a 9000 ppm concentration (e.g., 0.9% by weight) of this LBEA.

Comparative Example 9 (C9)

This nonwoven was produced on the above pilot line using CP360H polypropylene polymer at a throughput of 0.51 ghm. The belt speed was set to produce a basis weight of about 60 gsm for this sample.

Example 21 (E21)

This nonwoven was produced on the above pilot line using a throughput of 0.51 ghm using a blend of CP360H polypropylene polymer and a behenamide masterbatch mixed in proportions selected to get a 2000 ppm concentration (e.g., 0.2% by weight) of this LBEA in the formulation fed to the extruder of the pilot line. The belt speed was set to produce a basis weight of about 60 gsm for this sample.

Example 22 (E22)

This sample was produced in a similar way to Example 21 with the exception that enough behenamide masterbatch was added to achieve a 4000 ppm concentration (e.g., 0.4% by weight) of this LBEA.

Example 23 (E23)

This sample was produced in a similar way to Example 21 with the exception that enough behenamide masterbatch was added to achieve a 9000 ppm concentration (e.g., 0.9% by weight) of this LBEA.

Example 24 (E24)

This nonwoven was produced on the above pilot line using a throughput of 0.51 ghm using a blend of CP360H polypropylene polymer and an ethylene bis-oleamide masterbatch mixed in proportions selected to get a 2000 ppm concentration (e.g., 0.2% by weight) of this LBEA fed to the extruder of the pilot line. The belt speed was set to produce a basis weight of about 60 gsm for this sample.

Example 25 (E25)

This sample was produced in a similar way to Example 24 with the exception that enough ethylene bis-oleamide masterbatch was added to achieve a 4000 ppm concentration (e.g., 0.4% by weight) of this LBEA.

Example 26 (E26)

This sample was produced in a similar way to Example 24 with the exception that enough ethylene bis-oleamide masterbatch was added to achieve a 9000 ppm concentration (e.g., 0.9% by weight) of this LBEA.

Example 27 (E27)

This nonwoven was produced on the above pilot line using a throughput of 0.51 ghm using a blend of CP360H polypropylene polymer and an erucamide masterbatch mixed in proportions selected to get a 9000 ppm concentration (e.g., 0.9% by weight) of this LBEA fed to the extruder of the pilot line. The belt speed was set to produce a basis weight of about 60 gsm for this sample.

The process conditions can be found in Table 4 while the test results for the comparative and inventive examples can be found in Table 5.

As there were variations of basis weight between the samples made from the different formulations, we have therefore normalized the air permeability as well as the LSTST to a nominal basis weight; the latter being the basis weight that was targeted to achieve. That is, the normalized air permeability or the normalized LSTST is the relevant value we predict having if the samples had been at the nominal basis weight. Equation A, as shown below, was used to calculate the normalized LSTST while Equation B, as shown below, was used to calculate the normalized air permeability.

Normalized LSTST=LSTST*(Nominal basis weight/Actual basis weight);   Equation A:

where LSTST is in seconds and the basis weights are in gsm.

Normalized air permeability=Air Permeability*(Actual basis weight/nominal basis weight);   Equation B:

where the air permeability is in meter per minute (m/min) and the basis weights are in gsm.

These results clearly show how the addition of even 2000 ppm or more of behenamide improved LSTST in the majority of the cases, while the ethylene bis-oleamide showed improvement in LSTST at concentration of 4000 and 9000 ppm. These gains are even more evident when the LSTST It was also observed that behenamide produced a greater increase in LSTST than erucamide or ethylene bis-oleamide. While wishing not to be bound by the following theory, it is believed that a significant difference between behenamide and the two other amides used is the fact that behenamide is a saturated amide while erucamide and ethylene bis-oleamide are unsaturated amides. In this regard, it is currently believed that the presence of the unsaturation impacts the spatial arrangement of those molecules and modifies how they affect the repellency of the surface. It can be noted that this difference also impacts how such molecules affect the coefficient of friction (COF). The addition, for instance, of behenamide is known to have modest impact on COF of polyolefin film to which it is added, while erucamide is known to significantly reduce the COF of a polyolefin film when added at sufficient concentration.

TABLE 4

| Process condition | Unit | Value |
|---|---|---|
| Throughput targeted | ghm | 0.51 |
| Extruder Zone 1 temperature | ° C. | 210 |
| Extruder Zone 2 temperature | ° C. | 220 |
| Extruder Zone 3 temperature | ° C. | 230 |
| Spinneret block temperature | ° C. | 240 |
| Draw roll speed | rpm | 3605 |
| Calender rolls surface temperature | ° C. | 138 |
| Average die pressure | psi | 535 |

TABLE 5

| | LBEA | LBEA concentration ppm | Basis Weight gsm | Average fiber diameter micron | Average denier g/9000 l.m. | MFPD micron | Hydrohead mBar | LSTST sec | Normalized LSTST sec | Air Permeability m/min | Normalized air permeability m/min |
|---|---|---|---|---|---|---|---|---|---|---|---|
| C7 | none | 0 | 30.5 | | | 51 | 11.3 | 6.9 | 5.7 | 91 | 112 |
| E9 | LBEA-1 | 2000 | 24.8 | | | 47 | 8.9 | 6.2 | 6.2 | 138 | 136 |
| E10 | LBEA-1 | 4000 | 25 | | | 53 | 7.8 | 7.3 | 7.3 | 153 | 153 |
| E11 | LBEA-1 | 9000 | 25.2 | | | 85 | 8.1 | 8.4 | 8.3 | 141 | 143 |
| E12 | LBEA-2 | 2000 | 24.5 | | | 82 | 7.7 | 5.5 | 5.6 | 159 | 156 |
| E13 | LBEA-2 | 4000 | 24.2 | | | 84 | 6.4 | 6.4 | 6.6 | 180 | 174 |
| E14 | LBEA-2 | 9000 | 25.1 | | | 94 | 6.8 | 6.2 | 6.2 | 169 | 170 |
| C8 | | 0 | 44.9 | 16.3 | 1.71 | 32 | 16.5 | 15.5 | 15.5 | 40 | 40 |
| E15 | LBEA-1 | 2000 | 43.5 | | | 35 | 16.9 | 18.0 | 18.7 | 44 | 42 |
| E16 | LBEA-1 | 4000 | 43.1 | | | 29 | 17.5 | 21.7 | 22.7 | 45 | 43 |
| E17 | LBEA-1 | 9000 | 45.7 | 17.2 | 1.9 | 40 | 18.2 | 27.4 | 27.0 | 38 | 38 |
| E18 | LBEA-2 | 2000 | 46.2 | | | 54 | 16.6 | 15.1 | 14.7 | 41 | 42 |
| E19 | LBEA-2 | 4000 | 44.6 | | | 43 | 17.3 | 21.2 | 21.4 | 44 | 44 |
| E20 | LBEA-2 | 9000 | 45.2 | 17.2 | 1.9 | 55 | 15.7 | 19.6 | 19.5 | 45 | 45 |
| C9 | | 0 | 66.2 | | | 21 | 24.2 | 29.6 | 26.8 | 11 | 12 |
| E21 | LBEA-1 | 2000 | 60.3 | | | 19 | 24.6 | 44.3 | 44.1 | 14 | 14 |
| E22 | LBEA-1 | 4000 | 60.8 | | | 27 | 23.9 | 42.2 | 41.6 | 15 | 16 |
| E23 | LBEA-1 | 9000 | 62.9 | | | 33 | 23 | 63.4 | 60.5 | 14 | 15 |
| E24 | LBEA-2 | 2000 | 62.4 | | | 29 | 23.5 | 26.4 | 25.4 | 19 | 20 |
| E25 | LBEA-2 | 4000 | 61.3 | | | 28 | 21.6 | 37.2 | 36.4 | 25 | 26 |
| E26 | LBEA-2 | 9000 | 62.6 | | | 40 | 22.1 | 40.7 | 39.0 | 27 | 28 |
| E27 | LBEA-3 | 9000 | 54.1 | | | 29 | 19 | 31.2 | 34.6 | 31 | 28 | values are normalized based on basis weight. These gains are not matched by systematic equivalent reduction in air permeability or reduction of MFPD. Therefore, without being bonded by theory, it is believed that these results indicate that the impact of the LBEAs is through modification to the repellency properties of the fiber surface rather than impacting positively the structure of the nonwoven.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A nonwoven fabric, comprising: a plurality of nonwoven layers including (i) a first outermost layer consisting of non-round cross-sectional first layer continuous fibers all formed from a single homogeneous composition, (ii) a second outermost layer, and (iii) one or more interior layers between the first outermost layer and the second outermost layer; wherein the first outermost layer, the second outermost layer, and at least one of the one or more interior layers is defined by a respective plurality of fibers formed from a respective composition consisting of a polymer component and an additive component, the polymer component consisting of a polymer or polymeric blend consisting of a polypropylene homopolymer, a polyethylene, a polyester, a polyamide, or any combination thereof, and the additive component including a liquid-barrier-enhancing-agent (LBEA) consisting of erucamide, oleamide, strearamide, behenamide, one or more bis-amides, oleyl palmitamide, strearyl erucamide, or any combination thereof.

2. The nonwoven fabric of claim 1, wherein the LBEA is ethylene bis-strearamide, ethylene bis-oleamide, or a combination thereof.

3. The nonwoven fabric of claim 1, wherein the non-round cross-sectional first layer continuous fibers has a first average fiber diameter and the second outermost layer comprises a third nonwoven layer comprising a plurality of third layer fibers having a third average diameter, and the one or more internal layers includes a second nonwoven layer comprising a plurality of second layer fibers having a second average fiber diameter, and wherein the first average fiber diameter and the third average diameter both being larger than the second average fiber diameter.

4. The nonwoven fabric of claim 3, wherein the first outermost layer, the third nonwoven layer, or both comprise a spunbond nonwoven.

5. The nonwoven fabric of claim 4, wherein the second nonwoven layer comprises a meltblown nonwoven.

6. The nonwoven fabric of claim 1, wherein the nonwoven fabric comprises a construction according to one of the following formulae:

$$R1_a\text{-}M_b\text{-}N_c\text{-}R2_d; \quad (I)$$

wherein
  'M' comprises a meltblown nonwoven;
  'N' comprises a sub-micron fiber containing nonwoven or a fine fiber containing nonwoven prepared by a method other than meltblowing;
  'R1' comprises a spunbond nonwoven consisting of non-round cross-sectional fibers;
  'R2' comprises a spunbond nonwoven consisting of non-round cross-sectional fibers;
  'a' is independently selected from 1-5;
  'b' is independently selected from 0-8;
  'c' is independently selected from 0-3; and
  'd' is independently selected from 1-5;
wherein the sum of 'b' and 'c' is at least 1.

7. The nonwoven fabric of claim 1, wherein the nonwoven fabric comprises a construction according to the following formula:

$$(R1_a\text{-}S1_b)\text{-}M_c\text{-}N_d\text{-}(R2e\text{-}S2f \text{ or } S2r\text{-}R2e); \quad (III)$$

wherein
  'R1' comprises a spunbond nonwoven consisting of non-round cross-sectional fibers;
  'R2' comprises a spunbond nonwoven consisting of non-round cross-sectional fibers;
  'S1' comprises a spunbond nonwoven or a staple fiber-containing nonwoven comprising round cross-sectional fibers;
  'S2' comprises a spunbond nonwoven or a staple fiber-containing nonwoven comprising round cross-sectional fibers;
  'M' comprises a meltblown nonwoven;
  'N' comprises a sub-micron fiber containing nonwoven or a fine fiber containing nonwoven prepared by a method other than meltblowing;
  'a' is independently selected from 1-5;
  'b' is independently selected from 1-5;
  'c' is independently selected from 0-8;
  'd' is independently selected from 0-3;
  'e' is independently selected from 1-5; and
  'f' is independently selected from 1-5;
wherein the sum of 'c' and 'd' is at least 1.

8. The nonwoven fabric of claim 1, wherein the nonwoven fabric comprises a low surface tension strike through (LSTST) value that is greater than a comparative nonwoven fabric having the same construction except for being devoid of the LBEA.

9. The nonwoven fabric of claim 1, wherein the nonwoven fabric comprises a low surface tension strike through (LSTST) value that is from about 10% to about 60% greater than a comparative nonwoven fabric having the same construction except for being devoid of the LBEA.

10. The nonwoven fabric of claim 1, wherein the nonwoven fabric comprises a low surface tension strike through (LSTST) value from about 10 to about 80 seconds.

11. The nonwoven of claim 1, wherein the LBEA comprises a decomposition temperature as measured by thermogravimetric analysis (TGA) comprising from about 250° C. to about 380° C.; and wherein the plurality of nonwoven layers includes a first nonwoven layer comprising a plurality of first layer fibers having a first average fiber diameter and a second nonwoven layer comprising a plurality of second layer fibers having a second average fiber diameter, the first average fiber diameter being larger than the second average fiber diameter.

12. The nonwoven of claim 11, wherein the second nonwoven layer comprises an interior portion of the nonwoven fabric and is directly or indirectly sandwiched between the first nonwoven layer and a third nonwoven layer; wherein the first layer fibers comprise spunmelt fibers comprising a non-round cross-section.

13. The nonwoven of claim 11, wherein the second nonwoven layer comprises one or more meltblown layers comprising an interior portion of the nonwoven fabric and is directly or indirectly sandwiched between the first nonwoven layer and a third nonwoven layer; wherein at least one of the first nonwoven layer and the third nonwoven layer comprises a spunbond nonwoven comprising fibers comprising a non-round cross-section.

14. The nonwoven of claim 13, wherein second nonwoven layer includes the LBEA at a concentration from about 2000 to about 9000 ppm.

15. The nonwoven of claim 14, wherein the interior portion of the nonwoven fabric further comprises a sub-micron fiber containing nonwoven.

16. An article, comprising: a nonwoven fabric according to claim 1; wherein the article comprises a facemask, a surgical gown, a surgical drape, a lab coat, filter, or an absorbent article.

17. The nonwoven fabric of claim 1, wherein the one or more interior layers comprises a meltblown nonwoven comprising a plurality of meltblown fibers having an average diameter of less than 4 microns, and the second outermost layer consists of non-round cross-sectional continuous fibers.

18. The nonwoven fabric of claim 1, wherein the one or more interior layers comprises melt film fibrillated fibers.

19. The nonwoven fabric of claim 1, wherein the LBEA consists of behenamide.

* * * * *

UNITED STATES PATENT AND TRADEMARK OFFICE
CERTIFICATE OF CORRECTION

| | | |
|---|---|---|
| PATENT NO. | : 11,827,001 B2 | Page 1 of 1 |
| APPLICATION NO. | : 15/441780 | |
| DATED | : November 28, 2023 | |
| INVENTOR(S) | : Ralph A. Moody, III et al. | |

It is certified that error appears in the above-identified patent and that said Letters Patent is hereby corrected as shown below:

In the Claims

In Column 35, Claim 7, Line 67, "$(R1_a\text{-}S1_b) - M_c\text{-}N_d\text{-} (R2e\text{-}S2_f \text{ or } S2_f\text{-}R2_e)$" should read
--$(R1_a\text{-}S1_b) - M_c\text{-}N_d\text{-} (R2e\text{-}S2_f \text{ or } S2_f\text{-}R2_e)$--

Signed and Sealed this
Thirteenth Day of August, 2024

Katherine Kelly Vidal
*Director of the United States Patent and Trademark Office*